US012121500B2

(12) United States Patent
Tavis et al.

(10) Patent No.: US 12,121,500 B2
(45) Date of Patent: Oct. 22, 2024

(54) INHIBITORS OF BUNYAVIRIDAE AND USES THEREOF

(71) Applicants: Saint Louis University, St. Louis, MO (US); Research Foundation of The City University of New York, New York, NY (US)

(72) Inventors: John Edwin Tavis, Kirkwood, MO (US); Amelia Pinto, St. Louis, MO (US); James Brien, St. Louis, MO (US); Ryan Murelli, Belleville, NJ (US)

(73) Assignees: Saint Louis University, St. Louis, MO (US); Research Foundation of the City University of New York, New York, NY (US)

( * ) Notice: Subject to any disclaimer, the term of this patent is extended or adjusted under 35 U.S.C. 154(b) by 68 days.

(21) Appl. No.: 17/318,329

(22) Filed: May 12, 2021

(65) Prior Publication Data

US 2021/0393548 A1 Dec. 23, 2021

Related U.S. Application Data

(60) Provisional application No. 63/023,576, filed on May 12, 2020.

(51) Int. Cl.
*A61K 31/122* (2006.01)
*A61K 31/165* (2006.01)
*A61K 31/215* (2006.01)
*A61K 31/341* (2006.01)
*A61K 31/381* (2006.01)
*A61K 31/4412* (2006.01)
*A61K 31/454* (2006.01)
*A61P 31/14* (2006.01)

(52) U.S. Cl.
CPC .......... *A61K 31/122* (2013.01); *A61K 31/165* (2013.01); *A61K 31/215* (2013.01); *A61K 31/341* (2013.01); *A61K 31/381* (2013.01); *A61K 31/4412* (2013.01); *A61K 31/454* (2013.01); *A61P 31/14* (2018.01)

(58) Field of Classification Search
CPC .. A61K 31/122; A61K 31/165; A61K 31/215; A61K 31/341; A61K 31/381; A61K 31/4412; A61K 31/454; A61P 31/14
See application file for complete search history.

(56) References Cited

FOREIGN PATENT DOCUMENTS

KR 20200026390 * 3/2020 ............ A61K 31/35

OTHER PUBLICATIONS

Machine translation of KR 20200026390, Obtained from KIPO, accessed Apr. 22, 2023.*
Agyemang et al., "Divergent synthesis of a thiolate-based α-hydroxytropolone library with a dynamic bioactivity profile", *RSC Adv.*, 9:34227-34234, 2019.
Amroun et al., "Bunyaviridae RdRps: structure, motifs, and RNA synthesis machinery", Crit Rev Microbiol., 43(6):753-778, Nov. 2017.
Ariza et al., "Nucleocapsid protein structures from orthobunyaviruses reveal insight into ribonucleoprotein architecture and RNA polymerization", *Nuc. Acid Res.*, 41(11):5912-5926, 2013.
Berkowitz et al., "Amidation strategy for final-step α-hydroxytropolone diversification", *Tetrahedron Lett.*, 59:3026-3028, 2018.
Brooks et al., "Integrase Inhibitors: After 10 Years of Experience, Is the Best Yet to Come?", *Pharmacotherapy*, 39:576-598, 2019.
Cao et al., *ACS Omega*, 3:15125-15133, 2018.
Donlin et al., "Troponoids Can Inhibit Growth of the Human Fungal Pathogen Cryptococcus neoformans", *Antimicrob. Agents Chemother.*, 61:e02574-02516, 2017.
Edwards et al., "Inhibition of HBV replication by N-hydroxyisoquinolinedione and N-hydroxypyridinedione ribonuclease H inhibitors", *Antiviral Res.*, 164:70-80, 2019.
Edwards et al., "Shedding light on RNaseH: a promising target for hepatitis B Virus (HBV)", *Expert Opin. Ther. Targets*, 23(7):559-563, 2019.
2017 Annual Report of the Federal Select Agents Program.
Guo et al., "Characterization of the intracellular deproteinized relaxed circular DNA of hepatitis B virus: an intermediate of covalently closed circular DNA formation", *J. Virol.*, 81:12472-12484, 2007.

(Continued)

*Primary Examiner* — Alicia L Otton
(74) *Attorney, Agent, or Firm* — Parker Highlander PLLC

(57) ABSTRACT

The present disclosure provides inhibitors of bunyavirus of the formula:

(I)

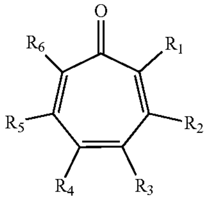

or (II)

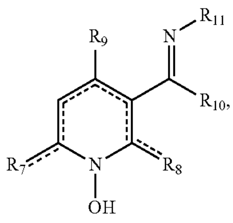

wherein the variables are defined herein. These inhibitors may be used to treat an infection of Rift Valley phlebovirus, hantavirus, and La Crosse virus, or Crimean-Congo Hemorrhagic fever.

17 Claims, 3 Drawing Sheets

(56) References Cited

OTHER PUBLICATIONS

Hartman, "Rift Valley Fever", *Clin. Lab. Med.*, 37:285-301, 2017.
Himmel et al., "Structure of HIV-1 Reverse Transcriptase with the Inhibitor β-Thujaplicinol Bound at the RNase H Active Site", *Structure,* 17:1625-1635, 2009.
Hirsch et al., "Synthesis and Biological Assessment of 3,7-Dihydroxytropolones", *Bioorg. Med. Chem. Lett.,* 24:4943-4947, 2014.
Hirsch et al., "Synthesis and biological assessment of 3,7-dihydroxytropolones", *Org. Biomol. Chem.,* 16:62-69, 2017.
Jacobsen et al., "Characterization and evaluation of pyrone and tropolone chelators for use in metalloprotein inhibitors", *Inorg. Chim. Acta,* 360(1):264-272, 2007.
Li, Qilan, et al. "Amide-containing α-hydroxytropolones as inhibitors of hepatitis B virus replication." *Antiviral research* 177 (2020): 104777.
Lomonosova et al., "Efficacy and cytotoxicity in cell culture of a novel α-hydroxytropolone inhibitors of hepatitis B virus ribonuclease H", *Antiviral Res.,* 144:164-172, 2017.
Lu et al., "Hydroxylated Tropolones Inhibit Hepatitis B Virus Replication by Blocking Viral Ribonuclease H Activity", *Antimicrob. Agents Chemother.,* 59:1070-1079, 2015.
Masaoka et al., "Characterization of the C-Terminal Nuclease Domain of Herpes Simplex Virus pUL15 as a Target of Nucleotidyltransferase Inhibitors", *Biochemistry,* 55:809-819, 2016.
Meck et al., "The biology and synthesis of α-hydroxytropolones", *MedChemComm,* 5, 842-852, 2014.
Meck et al., "An Oxidopyrylium Cyclization/Ring-Opening Route to Polysubstituted α-Hydroxytropolones", *Org. Lett.,* 14:5988-5991, 2012.
Mehand et al., "The WHO R&D Blueprint: 2018 review of emerging infectious diseases requiring urgent research and development efforts", *Antiviral Res.,* 159:63-67, 2018.
Olschewski, Silke, Stephen Cusack, and Maria Rosenthal. "The cap-snatching mechanism of Bunyaviruses." *Trends in microbiology* 28.4 (2020): 293-303.
Omoto et al., "Characterization of influenza virus variants induced by treatment with the endonuclease inhibitor baloxavir marboxil", *Sci. Rep.,* 8:9633, 2018.
Suchaud et al., "Development of a series of 3-hydroxyquinolin-2(1H)-ones as selective inhibitors of HIV-1 reverse transcriptase associated RNase H activity", *Bioorg. Med. Chem. Lett.,* 22:3988-3992, 2012.
Tavis et al., "The hepatitis B virus ribonuclease H is sensitive to inhibitors of the human immunodeficiency virus ribonuclease H and integrase enzymes", *PLoS Pathog,* 9:e1003125, 2013.
Villa et al., "Purification and enzymatic characterization of the hepatitis B virus ribonuclease H, a new target for antiviral inhibitors", *Antiviral Res.,* 132:186-195, 2016.
Wang et al., "Update on Recent Developments in Small Molecular HIV-1 RNase H Inhibitors (2013-2016): Opportunities and Challenges", *Curr. Med. Chem.,* 25:1682-1702, 2018.
Soldan et al., "The Bunyaviridae, Chapter 21", *Handbook of Clinical Neurology*, vol. 123, 2014.

* cited by examiner

α-Hydroxytropolones

308

359

362

694

Tropolones

340

341

Thiotropolones

680

686

N-Hydroxypyridinediones

517

518

668

670

Dihydronapthalene

327

INHIBITORS OF BUNYAVIRIDAE AND USES THEREOF

This application claims the benefit of priority to U.S. Provisional Application No. 63/023,576, filed on May 12, 2020, the entire contents of which are hereby incorporated by reference.

GOVERNMENT SUPPORT CLAUSE

This invention was made with government support under Grant No. R01 AI122669 awarded by the National Institutes of Health. The government has certain rights in the invention.

BACKGROUND

I. Field

The disclosure relates to the fields of pathology, virology, molecular biology and pharmaceuticals. More specifically, the disclosure relates to inhibitors for the treatment and prevention of diseases associated with an infection of viruses within the Bunyaviridae family.

II. Related Art

Rift Valley Fever Virus (RVFV) is an enveloped virus with a segmented, negative-polarity, single-stranded RNA genome (Hartman, 2017). It is a member of the formerly defined Bunyaviridae family of viruses that also includes Hantaan Virus, La Crosse Virus, and Crimean-Congo Hemorrhagic Fever Virus (Amroun et al., 2017). Recently, Bunyaviridae has been combined with the related Arenaviridae family to form a new taxon, the Bunyvirales order. RVFV is an arbovirus transmitted to animals by mosquito vectors that is traditionally endemic in eastern and southern Africa, but it has recently expanded it range throughout sub-Saharan Africa. RVFV is a serious veterinary pathogen, causing Rift Valley Fever in domestic animals including cattle, horses, sheep, goats, and camels. Rift Valley Fever causes diseases associated with fever, hemorrhage, diarrhea, death, and spontaneous abortions in infected animals, and often has severe economic impacts on affected herds. Veterinary outbreaks of RVFV infections can reach epidemic proportions, particularly in especially rainy years.

Humans can be infected by RVFV via contact with infected animal body fluids or tissues, by breathing aerosols contaminated with RVFV, or less frequently via mosquito bites, but human to human transmission is rare (Hartman, 2017). Most infections are either asymptomatic or cause mild fever with hepatic involvement. However, 8-10% of infections are severe, where symptoms can include lesions to the eye causing blindness in 50% of ocular cases (1-10% of all infections), encephalitis, gastrointestinal dysfunction, jaundice, joint/muscle pain, hemorrhagic fever, disorientation/hallucination, and partial paralysis. Hemorrhagic fever is rare (~1% of cases) but has a ~50% fatality rate. Human RVFV infections can be diagnosed by ELISA or RT-PCR assays, but treatment is limited to supportive care (Hartman, 2017). There is a veterinary vaccine for RVFV but none for humans.

RVFV and CCHFV are among the emerging viral pathogens for which there are insufficient or inadequate medical treatments, or pipelines to develop them, that were highlighted in the 2018 World Health Organization research and development blueprint for high priority targets (Mehand et al., 2018). Both RVFV and CCHFV are listed by the American government as select agents of significant concern as biowarfare threats (Federal Select Agents Program, 2017).

Compounds that inhibit Bunyaviridae such as RVFV are still need to treat this emerging viral threat.

SUMMARY

Thus, in accordance with the present disclosure, there is provided compounds useful for inhibiting Bunyaviridae such as Rift Valley fever virus.

In some aspects, the present disclosure provides methods of treating Rift Valley fever in a patient comprising administering to the patient a therapeutically effective amount of a compound according to the formula:

(I)

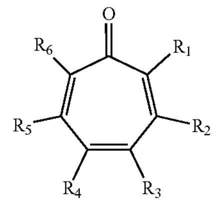

wherein:

$R_1$ is hydrogen or hydroxy; or a group of the formula: $SC(O)R_1'$, wherein:

$R_1'$ is an amino acid residue, a protected amino acid residue, aryl$_{(C\leq12)}$, heteroaryl$_{(C\leq12)}$, aralkyl$_{(C\leq12)}$, or a substituted version of these three groups $R_2$ or $R_5$ are each independently selected from hydrogen, halo, hydroxy, aryl$_{(C\leq12)}$, substituted aryl$_{(C\leq12)}$, acyl$_{(C\leq12)}$, substituted acyl$_{(C\leq12)}$, —C(O)R', or —S(O)$_x$R'', wherein:

R' is —$X_1$—$Y_1$, wherein:

$X_1$ is alkanediyl$_{(C\leq8)}$, alkenediyl$_{(C\leq8)}$, or a substituted version thereof; and $Y_1$ is aryl$_{(C\leq12)}$, heteroaryl$_{(C\leq12)}$, or a substituted version thereof;

x is 0, 1, or 2;

R'' is alkyl$_{(C\leq12)}$, aryl$_{(C\leq12)}$, aralkyl$_{(C\leq12)}$, or a substituted version thereof;

$R_3$ is hydrogen, alkyl$_{(C\leq12)}$, or substituted alkyl$_{(C\leq12)}$;

$R_4$ is hydrogen or alkyl$_{(C\leq12)}$, cycloalkyl$_{(C\leq12)}$, aryl$_{(C\leq18)}$, heteroaryl$_{(C\leq18)}$, or a substituted version of these four groups; —C(O)$R_a$, —S(O)$_y$$R_b$, —C(O)N($R_c$)$R_d$, or

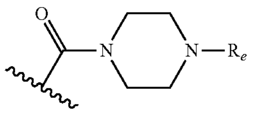

wherein:

$R_a$ is alkyl$_{(C\leq12)}$, cycloalkyl$_{(C\leq12)}$, aryl$_{(C\leq12)}$, heteroaryl$_{(C\leq12)}$, heterocycloalkyl$_{(C\leq12)}$, alkoxy$_{(C\leq12)}$, or —$X_2$—$Y_2$, wherein:

$X_2$ is arenediyl$_{(C\leq12)}$ or substituted arenediyl$_{(C\leq12)}$; and $Y_2$ is aryl$_{(C\leq12)}$, heteroaryl$_{(C\leq12)}$, or a substituted version thereof;

$R_b$ is aryl$_{(C\leq12)}$, heteroaryl$_{(C\leq12)}$, or a substituted version thereof;

$R_c$ is hydrogen, alkyl$_{(C\leq6)}$, or substituted alkyl$_{(C\leq6)}$;

$R_d$ is alkyl$_{(C\leq12)}$, cycloalkyl$_{(C\leq12)}$, aryl$_{(C\leq12)}$, heteroaryl$_{(C\leq12)}$, aralkyl$_{(C\leq12)}$, heterocycloalkyl$_{(C\leq12)}$, or a substituted version thereof, or —$X_3$—$Y_3$;

wherein:

$X_3$ is arenediyl$_{(C\leq12)}$, alkanediyl$_{(C\leq8)}$-arenediyl$_{(C\leq12)}$, or a substituted version thereof; and $Y_3$ is aryl$_{(C\leq12)}$, heteroaryl$_{(C\leq12)}$, aralkyl$_{(C\leq12)}$, heterocycloalkyl$_{(C\leq12)}$, aralkoxy$_{(C\leq12)}$, or a substituted version thereof;

$R_e$ is aryl$_{(C\leq12)}$, heteroaryl$_{(C\leq12)}$, aralkyl$_{(C\leq18)}$, or a substituted version thereof, or a group of the formula:

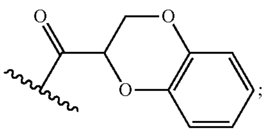

; and $R_6$ is hydrogen or hydroxy; or a compound of the formula:

(II)

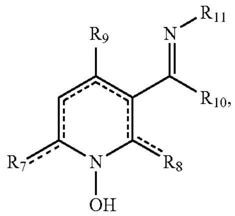

wherein:

$R_7$ and $R_8$ are each independently oxo or hydroxy;

$R_9$ and $R_{10}$ are each independently hydrogen, alkyl$_{(C\leq6)}$, or substituted alkyl$_{(C\leq6)}$; and $R_{11}$ is aryl$_{(C\leq12)}$, substituted aryl$_{(C\leq12)}$, or —$X_4$—$Y_4$;

wherein:

$X_4$ is arenediyl$_{(C\leq12)}$ or substituted arenediyl$_{(C\leq12)}$; and $Y_4$ is aryloxy$_{(C\leq12)}$ or substituted aryloxy$_{(C\leq12)}$;

or a pharmaceutically acceptable salt of either of these formulae.

In some embodiments, the compounds are further defined as:

(I)

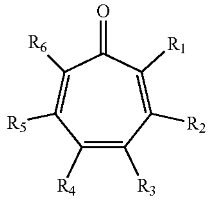

wherein:

$R_1$ is hydrogen or hydroxy; or a group of the formula: SC(O)$R_1'$, wherein:

$R_1'$ is an amino acid residue, a protected amino acid residue, aryl$_{(C\leq12)}$, heteroaryl$_{(C\leq12)}$, aralkyl$_{(C\leq12)}$, or a substituted version of these three groups $R_2$ or $R_5$ are each independently selected from hydrogen, halo, hydroxy, aryl$_{(C\leq12)}$, substituted aryl$_{(C\leq12)}$, acyl$_{(C\leq12)}$, substituted acyl$_{(C\leq12)}$, —C(O)R', or —S(O)$_x$R", wherein:

R' is —$X_1$—$Y_1$, wherein:

$X_1$ is alkanediyl$_{(C\leq8)}$, alkenediyl$_{(C\leq8)}$, or a substituted version thereof; and $Y_1$ is aryl$_{(C\leq12)}$, heteroaryl$_{(C\leq12)}$, or a substituted version thereof;

x is 0, 1, or 2;

R" is alkyl$_{(C\leq12)}$, aryl$_{(C\leq12)}$, aralkyl$_{(C\leq12)}$, or a substituted version thereof;

$R_3$ is hydrogen, alkyl$_{(C\leq12)}$, or substituted alkyl$_{(C\leq12)}$;

$R_4$ is hydrogen or alkyl$_{(C\leq12)}$, cycloalkyl$_{(C\leq12)}$, aryl$_{(C\leq18)}$, heteroaryl$_{(C\leq18)}$, or a substituted version of these four groups; —C(O)$R_a$, —S(O)$_y$$R_b$, —C(O)N($R_c$)$R_d$, or

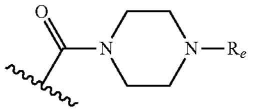

wherein:

$R_a$ is alkyl$_{(C\leq12)}$, cycloalkyl$_{(C\leq12)}$, aryl$_{(C\leq12)}$, heteroaryl$_{(C\leq12)}$, heterocycloalkyl$_{(C\leq12)}$, alkoxy$_{(C\leq12)}$, or —$X_2$—$Y_2$, wherein:

$X_2$ is arenediyl$_{(C\leq12)}$ or substituted arenediyl$_{(C\leq12)}$; and $Y_2$ is aryl$_{(C\leq12)}$, heteroaryl$_{(C\leq12)}$, or a substituted version thereof;

$R_b$ is aryl$_{(C\leq12)}$, heteroaryl$_{(C\leq12)}$, or a substituted version thereof;

$R_c$ is hydrogen, alkyl$_{(C\leq6)}$, or substituted alkyl$_{(C\leq6)}$;

$R_d$ is alkyl$_{(C\leq12)}$, cycloalkyl$_{(C\leq12)}$, aryl$_{(C\leq12)}$, heteroaryl$_{(C\leq12)}$, aralkyl$_{(C\leq12)}$, heterocycloalkyl$_{(C\leq12)}$, or a substituted version thereof, or —$X_3$—$Y_3$;

wherein:

$X_3$ is arenediyl$_{(C\leq12)}$, -alkanediyl$_{(C\leq8)}$-arenediyl$_{(C\leq12)}$, or a substituted version thereof; and $Y_3$ is aryl$_{(C\leq12)}$, heteroaryl$_{(C\leq12)}$, aralkyl$_{(C\leq12)}$, heterocycloalkyl$_{(C\leq12)}$, aralkoxy$_{(C\leq12)}$, or a substituted version thereof;

$R_e$ is aryl$_{(C\leq12)}$, heteroaryl$_{(C\leq12)}$, aralkyl$_{(C\leq18)}$, or a substituted version thereof, or a group of the formula:

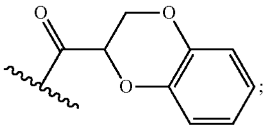

; and $R_6$ is hydrogen or hydroxy;

or a pharmaceutically acceptable salt thereof.

In some embodiments, the compounds are further defined as:

(I)

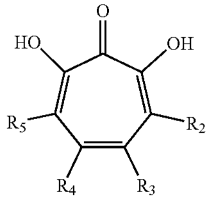

wherein:

- $R_2$ or $R_5$ are each independently selected from hydrogen, halo, hydroxy, aryl$_{(C\leq 12)}$, substituted aryl$_{(C\leq 12)}$, acyl$_{(C\leq 12)}$, substituted acyl$_{(C\leq 12)}$, —C(O)R', or —S(O)$_x$R", wherein:
  - R' is —$X_1$—$Y_1$, wherein:
    - $X_1$ is alkanediyl$_{(C\leq 8)}$, alkenediyl$_{(C\leq 8)}$, or a substituted version thereof; and
    - $Y_1$ is aryl$_{(C\leq 12)}$, heteroaryl$_{(C\leq 12)}$, or a substituted version thereof;
  - x is 0, 1, or 2;
  - R" is alkyl$_{(C\leq 12)}$, aryl$_{(C\leq 12)}$, aralkyl$_{(C\leq 12)}$, or a substituted version thereof;
- $R_3$ is hydrogen, alkyl$_{(C\leq 12)}$, or substituted alkyl$_{(C\leq 12)}$;
- $R_4$ is hydrogen or alkyl$_{(C\leq 12)}$, cycloalkyl$_{(C\leq 12)}$, aryl$_{(C\leq 18)}$, heteroaryl$_{(C\leq 18)}$, or a substituted version of these four groups; —C(O)$R_a$, —S(O)$_y$$R_b$, —C(O)N($R_c$)$R_d$, or

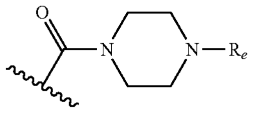

wherein:

- $R_a$ is alkyl$_{(C\leq 12)}$, cycloalkyl$_{(C\leq 12)}$, aryl$_{(C\leq 12)}$, heteroaryl$_{(C\leq 12)}$, heterocycloalkyl$_{(C\leq 12)}$, alkoxy$_{(C\leq 12)}$, or —$X_2$—$Y_2$, wherein:
  - $X_2$ is arenediyl$_{(C\leq 12)}$ or substituted arenediyl$_{(C\leq 12)}$; and
  - $Y_2$ is aryl$_{(C\leq 12)}$, heteroaryl$_{(C\leq 12)}$, or a substituted version thereof;
- $R_b$ is aryl$_{(C\leq 12)}$, heteroaryl$_{(C\leq 12)}$, or a substituted version thereof;
- $R_c$ is hydrogen, alkyl$_{(C\leq 6)}$, or substituted alkyl$_{(C\leq 6)}$;
- $R_d$ is alkyl$_{(C\leq 12)}$, cycloalkyl$_{(C\leq 12)}$, aryl$_{(C\leq 12)}$, heteroaryl$_{(C\leq 12)}$, aralkyl$_{(C\leq 12)}$, heterocycloalkyl$_{(C\leq 12)}$, or a substituted version thereof, or —$X_3$—$Y_3$; wherein:
  - $X_3$ is arenediyl$_{(C\leq 12)}$, alkanediyl$_{(C\leq 8)}$-arenediyl$_{(C\leq 12)}$, or a substituted version thereof; and
  - $Y_3$ is aryl$_{(C\leq 12)}$, heteroaryl$_{(C\leq 12)}$, aralkyl$_{(C\leq 12)}$, heterocycloalkyl$_{(C\leq 12)}$, aralkoxy$_{(C\leq 12)}$, or a substituted version thereof;
- $R_e$ is aryl$_{(C\leq 12)}$, heteroaryl$_{(C\leq 12)}$, aralkyl$_{(C\leq 18)}$, or a substituted version thereof, or a group of the formula:

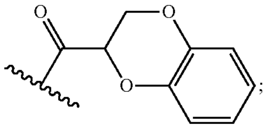

; and or a pharmaceutically acceptable salt thereof.

In some embodiments, $R_3$ is hydrogen. In other embodiments, $R_3$ is alkyl$_{(C\leq 12)}$ or substituted alkyl$_{(C\leq 12)}$. In further embodiments, $R_3$ is alkyl$_{(C\leq 12)}$, such as methyl. In some embodiments, $R_2$ is hydrogen. In other embodiments, $R_2$ is —S(O)$_x$R", wherein: R" is alkyl$_{(C\leq 12)}$, aryl$_{(C\leq 12)}$, aralkyl$_{(C\leq 12)}$, or a substituted version thereof. In some embodiments, R" is alkyl$_{(C\leq 12)}$ or substituted alkyl$_{(C\leq 12)}$. In further embodiments, R" is alkyl$_{(C\leq 12)}$. In still further embodiments, R" is methyl, isopropyl, butyl, or hexyl, such as butyl. In some embodiments, $R_5$ is hydrogen. In other embodiments, $R_5$ is halo, such as bromo. In still other embodiments, $R_5$ is aryl$_{(C\leq 12)}$ or substituted aryl$_{(C\leq 12)}$. In further embodiments, $R_5$ is aryl$_{(C\leq 12)}$, such as phenyl or napthyl. In yet other embodiments, $R_5$ is —S(O)$_x$R", wherein: R" is alkyl$_{(C\leq 12)}$, aryl$_{(C\leq 12)}$, aralkyl$_{(C\leq 12)}$, or a substituted version thereof. In some embodiments, R" is alkyl$_{(C\leq 12)}$ or substituted alkyl$_{(C\leq 12)}$. In further embodiments, R" is alkyl$_{(C\leq 12)}$. In still further embodiments, methyl, isopropyl, butyl, or hexyl, such as butyl. In some embodiments, $R_1$ is hydroxy. In some embodiments, $R_6$ is hydroxy.

In some embodiments, $R_4$ is —C(O)$R_a$, wherein:

- $R_a$ is alkyl$_{(C\leq 12)}$, cycloalkyl$_{(C\leq 12)}$, aryl$_{(C\leq 12)}$, heteroaryl$_{(C\leq 12)}$, alkyl$_{(C\leq 12)}$, alkoxy$_{(C\leq 12)}$, or —$X_2$—$Y_2$, wherein:
  - $X_2$ is arenediyl$_{(C\leq 12)}$ or substituted arenediyl$_{(C\leq 12)}$; and
  - $Y_2$ is aryl$_{(C\leq 12)}$, heteroaryl$_{(C\leq 12)}$, or a substituted version thereof.

In some embodiments, $R_a$ is alkyl$_{(C\leq 12)}$ or substituted alkyl$_{(C\leq 12)}$. In further embodiments, $R_a$ is alkyl$_{(C\leq 12)}$, such as methyl. In other embodiments, $R_a$ is aryl$_{(C\leq 12)}$ or substituted aryl$_{(C\leq 12)}$. In further embodiments, $R_a$ is aryl$_{(C\leq 12)}$, such as biphenyl. In some embodiments, $R_a$ is substituted aryl$_{(C\leq 12)}$, such as 2-hydroxyphenyl or 3-bromophenyl. In still other embodiments, $R_a$ is heterocycloalkyl$_{(C\leq 12)}$ or substituted heterocycloalkyl$_{(C\leq 12)}$. In further embodiments, $R_a$ is heterocycloalkyl$_{(C\leq 12)}$, such as piperidinyl. In yet other embodiments, $R_a$ is alkoxy$_{(C\leq 12)}$ or substituted alkoxy$_{(C\leq 12)}$. In further embodiments, $R_a$ is alkoxy$_{(C\leq 12)}$, such as methoxy.

In other embodiments, $R_4$ is —S(O)$_y$$R_b$, wherein: $R_b$ is aryl$_{(C\leq 12)}$, heteroaryl$_{(C\leq 12)}$, or a substituted version thereof. In further embodiments, aryl$_{(C\leq 12)}$ or substituted aryl$_{(C\leq 12)}$. In still further embodiments, $R_b$ is aryl$_{(C\leq 12)}$, such as phenyl.

In yet other embodiments, $R_4$ is —C(O)N($R_c$)$R_d$, wherein:

- $R_c$ is hydrogen, alkyl$_{(C\leq 6)}$, or substituted alkyl$_{(C\leq 6)}$;
- $R_d$ is alkyl$_{(C\leq 12)}$, cycloalkyl$_{(C\leq 12)}$, aryl$_{(C\leq 12)}$, heteroaryl$_{(C\leq 12)}$, aralkyl$_{(C\leq 12)}$, heterocycloalkyl$_{(C\leq 12)}$, or a substituted version thereof, or —$X_3$—$Y_3$; wherein:
  - $X_3$ is arenediyl$_{(C\leq 12)}$, -alkanediyl$_{(C\leq 8)}$-arenediyl$_{(C\leq 12)}$, or a substituted version thereof; and
  - $Y_3$ is aryl$_{(C\leq 12)}$, heteroaryl$_{(C\leq 12)}$, aralkyl$_{(C\leq 12)}$, heterocycloalkyl$_{(C\leq 12)}$, aralkoxy$_{(C\leq 12)}$, or a substituted version thereof.

In some embodiments, $R_c$ is hydrogen. In some embodiments, $R_d$ is alkyl$_{(C\leq 12)}$ or substituted alkyl$_{(C\leq 12)}$. In further embodiments, $R_d$ is alkyl$_{(C\leq 12)}$, such as butyl.

In other embodiments, $R_4$ is
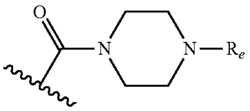
wherein:
$R_e$ is aryl$_{(C\leq12)}$, heteroaryl$_{(C\leq12)}$, aralkyl$_{(C\leq18)}$, or a substituted version thereof.
In some embodiments. $R_e$ is aralkyl$_{(C\leq18)}$ or substituted aralkyl$_{(C\leq18)}$. In further embodiments, $R_e$ is aralkyl$_{(C\leq18)}$, such as di-(4-fluorophenyl)methyl.
In some embodiments, the compound is further defined as:
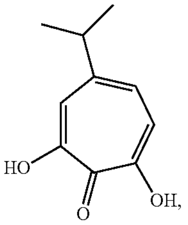
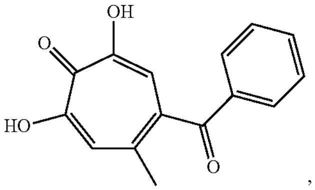
,
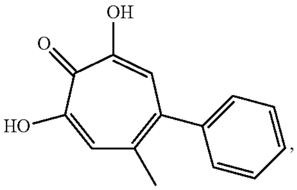
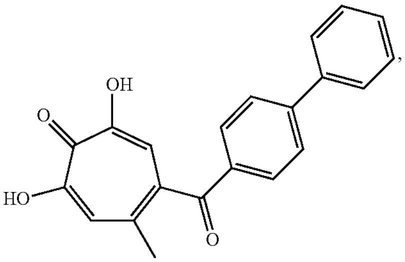
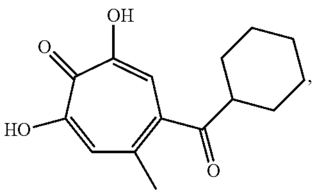
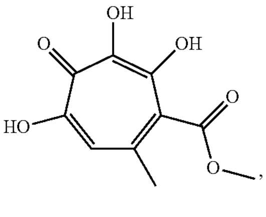
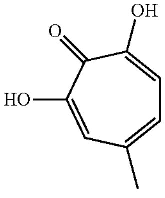
,
-continued
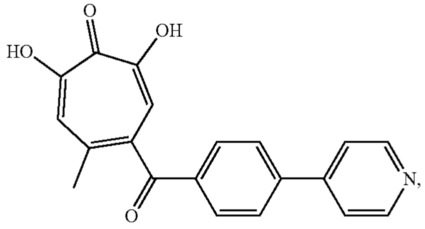
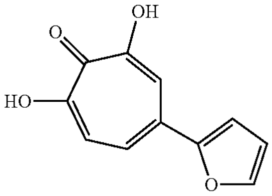
,
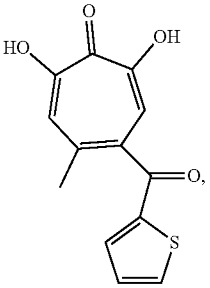
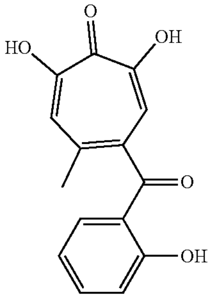
,
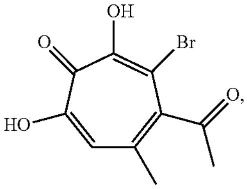
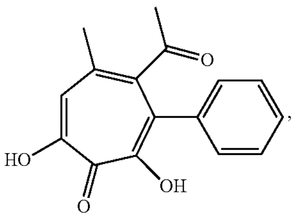
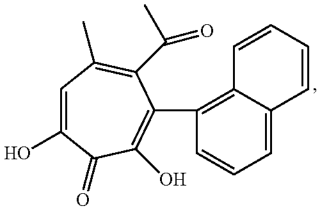
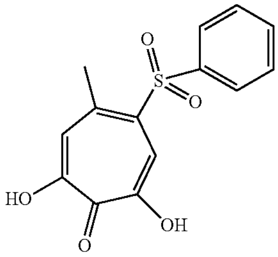
,
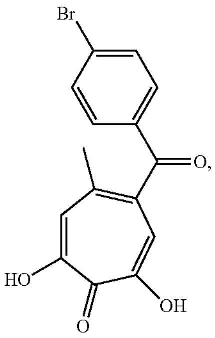

-continued
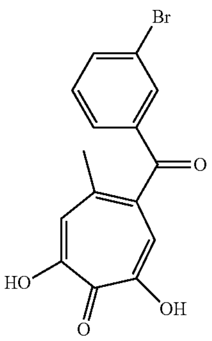
,
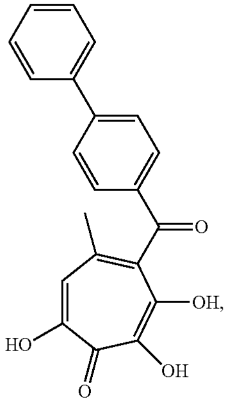
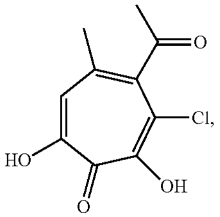
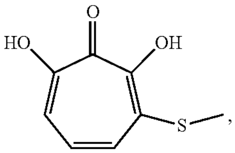
,
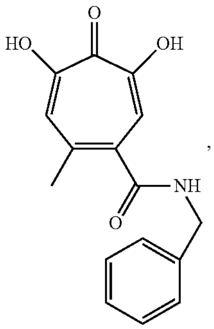
,
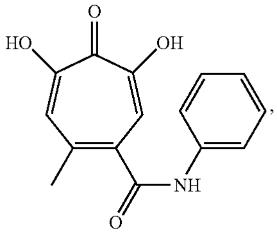
,
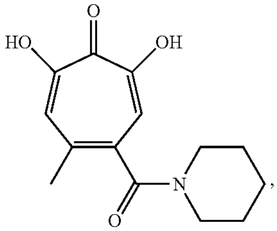
,
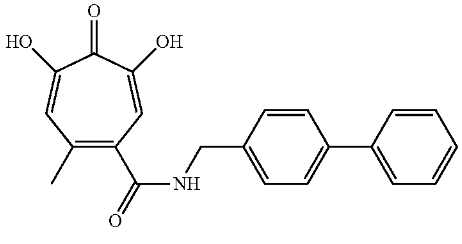
,
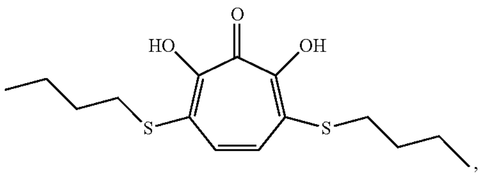
,
-continued
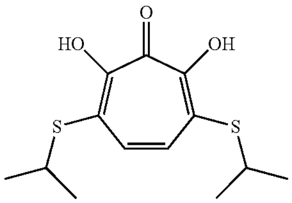
,
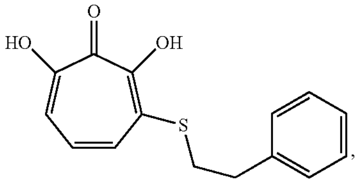
,
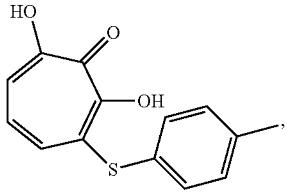
,
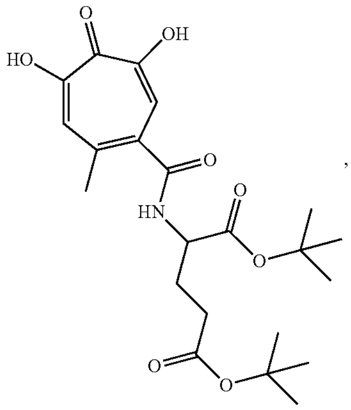
,
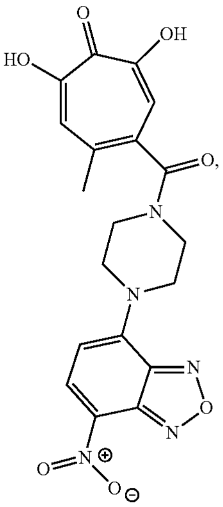
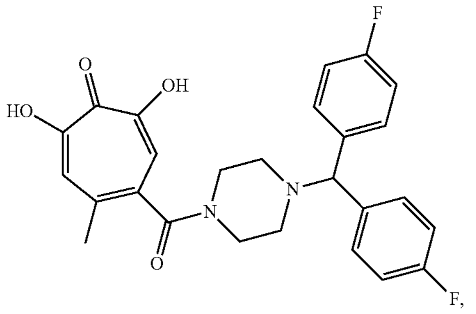
or
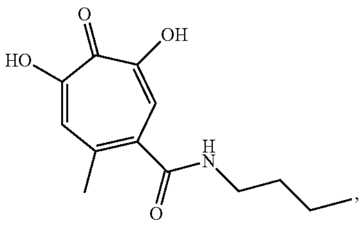
, -continued

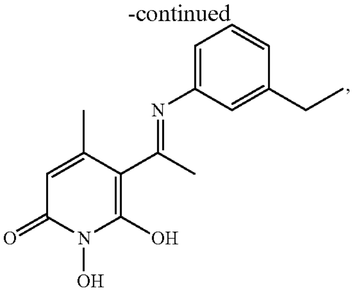

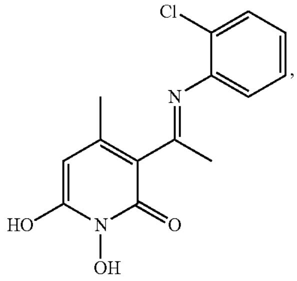

, or

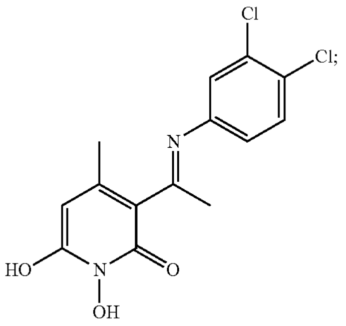

or a pharmaceutically acceptable salt thereof.

In some embodiments, the compound is administered intravenously, intraarterially, orally, buccally, nasally, ocularly, rectally, vaginally, topically, intramuscularly, intradermally, cutaneously, or subcutaneously. In some embodiments, the methods further comprise administering a second anti-viral therapy. In some embodiments, the anti-viral therapy is a vaccine for Rift Valley fever. In some embodiments, the anti-viral therapy is administered before the compound. In other embodiments, the anti-viral therapy is administered after the compound. In some embodiments, the patient is a mammal, such as a human. In other embodiments, the patient is a livestock animal, such as a cow, a horse, a sheep, a goat, or a camel.

In other aspects, the present disclosure provides methods of inhibiting the replication of a bunyavirus comprising contacting the cell with an effective amount of a compound according to the formula:

(I)

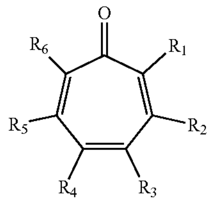

wherein:

$R_1$ is hydrogen or hydroxy; or a group of the formula: $SC(O)R_1'$, wherein:

$R_1'$ is an amino acid residue, a protected amino acid residue, aryl$_{(C\leq12)}$, heteroaryl$_{(C\leq12)}$, aralkyl$_{(C\leq12)}$, or a substituted version of these three groups $R_2$ or $R_5$ are each independently selected from hydrogen, halo, hydroxy, aryl$_{(C\leq12)}$, substituted aryl$_{(C\leq12)}$, acyl$_{(C\leq12)}$, substituted acyl$_{(C\leq12)}$, —C(O)R', or —$S(O)_xR''$, wherein:

R' is —$X_1$—$Y_1$, wherein:

$X_1$ is alkanediyl$_{(C\leq8)}$, alkenediyl$_{(C\leq8)}$, or a substituted version thereof; and $Y_1$ is aryl$_{(C\leq12)}$, heteroaryl$_{(C\leq12)}$, or a substituted version thereof;

x is 0, 1, or 2;

R'' is alkyl$_{(C\leq12)}$, aryl$_{(C\leq12)}$, aralkyl$_{(C\leq12)}$, or a substituted version thereof;

$R_3$ is hydrogen, alkyl$_{(C\leq12)}$, or substituted alkyl$_{(C\leq12)}$;

$R_4$ is hydrogen or alkyl$_{(C\leq12)}$, cycloalkyl$_{(C\leq12)}$, aryl$_{(C\leq18)}$, heteroaryl$_{(C\leq18)}$, or a substituted version of these four groups; —$C(O)R_a$, —$S(O)_yR_b$, —$C(O)N(R_c)R_d$, or

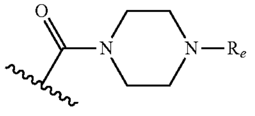

wherein:

$R_a$ is alkyl$_{(C\leq12)}$, cycloalkyl$_{(C\leq12)}$, aryl$_{(C\leq12)}$, heteroaryl$_{(C\leq12)}$, heterocycloalkyl$_{(C\leq12)}$, alkoxy$_{(C\leq12)}$, or —$X_2$—$Y_2$, wherein:

$X_2$ is arenediyl$_{(C\leq12)}$ or substituted arenediyl$_{(C\leq12)}$; and $Y_2$ is aryl$_{(C\leq12)}$, heteroaryl$_{(C\leq12)}$, or a substituted version thereof;

$R_b$ is aryl$_{(C\leq12)}$, heteroaryl$_{(C\leq12)}$, or a substituted version thereof;

$R_c$ is hydrogen, alkyl$_{(C\leq6)}$, or substituted alkyl$_{(C\leq6)}$;

$R_a$ is alkyl$_{(C\leq12)}$, cycloalkyl$_{(C\leq12)}$, aryl$_{(C\leq12)}$, heteroaryl$_{(C\leq12)}$, aralkyl$_{(C\leq12)}$, heterocycloalkyl$_{(C\leq12)}$, or a substituted version thereof, or —$X_3$—$Y_3$;

wherein:

$X_3$ is arenediyl$_{(C\leq12)}$, -alkanediyl$_{(C\leq8)}$-arenediyl$_{(C\leq12)}$, or a substituted version thereof; and $Y_3$ is aryl$_{(C\leq12)}$, heteroaryl$_{(C\leq12)}$, aralkyl$_{(C\leq12)}$, heterocycloalkyl$_{(C\leq12)}$, aralkoxy$_{(C\leq12)}$, or a substituted version thereof;

$R_e$ is aryl$_{(C\leq12)}$, heteroaryl$_{(C\leq12)}$, aralkyl$_{(C\leq18)}$, or a group of the formula:

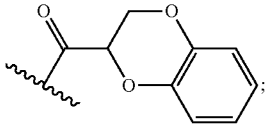

; and $R_6$ is hydrogen or hydroxy; or a compound of the formula:

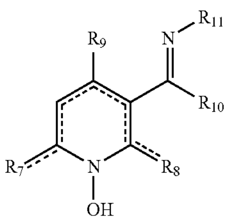

(II)

wherein:

$R_7$ and $R_8$ are each independently oxo or hydroxy;

$R_9$ and $R_{10}$ are each independently hydrogen, alkyl$_{(C\leq6)}$, or substituted alkyl$_{(C\leq6)}$; and $R_{11}$ is aryl$_{(C\leq12)}$, substituted aryl$_{(C\leq12)}$, or —$X_4$—$Y_4$; wherein:

$X_4$ is arenediyl$_{(C\leq12)}$ or substituted arenediyl$_{(C\leq12)}$;

$Y_4$ is aryloxy$_{(C\leq12)}$ or substituted aryloxy$_{(C\leq12)}$;

or a pharmaceutically acceptable salt of either of these formulae.

In some embodiments, the bunyavirus is Rift Valley phlebovirus. In other embodiments, the bunyavirus is orthohantavirus. In still other embodiments, the bunyavirus is La Crosse arbovirus. In yet other embodiments, the bunyavirus is Crimean-Congo hemorrhagic fever orthoairovirus. In some embodiments, the method is performed in vitro. In some embodiments, the method is performed in vivo. In other embodiments, the method is performed ex vivo. In some embodiments, the method is sufficient to treat Rift Valley fever in a patient. In some embodiments, the method is sufficient to treat an infection of hantavirus in a patient. In some embodiments, the method is sufficient to treat La Crosse encephalitis in a patient. In some embodiments, the method is sufficient to treat Crimean-Congo Hemorrhagic fever in a patient.

Other objects, features and advantages of the present disclosure will become apparent from the following detailed description. It should be understood, however, that the detailed description and the specific examples, while indicating preferred embodiments of the disclosure, are given by way of illustration only, since various changes and modifications within the spirit and scope of the disclosure will become apparent to those skilled in the art from this detailed description.

BRIEF DESCRIPTION OF THE FIGURES

The following drawings form part of the present specification and are included to further demonstrate certain aspects of the present disclosure. The disclosure may be better understood by reference to one or more of these drawings in combination with the detailed description.

DETAILED DESCRIPTION

Figure 1:
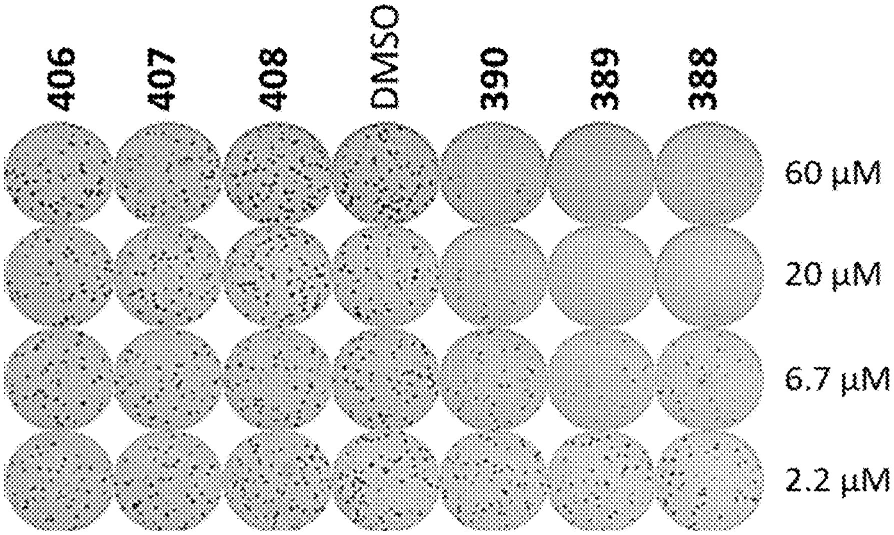
FIG. 1 shows an example primary screening assay. Primary screening data are shown for the DMSO vehicle control, inactive compounds (406, 407, 408), and compounds active the primary screen, (390, 389, and 388). RVFV foci are visible as dark spots, and the integrity of the cell monolayer indicating lack of overt cytotoxicity is shown by the uniform gray background staining of the cells in each well.

Provided herein are compounds which are useful for the treatment of an infection with a member of Bunyaviridae such as Rift Valley Fever, Crimean-Congo hemorrhagic fever, or La Crosse encephalitis virus. These details will be described in more detail.

A. BUNYAVIRIDAE

Bunyavirales is a newly defined order of viruses that combines the previously defined viral families Bunyaviridae and Arenaviridae. Rift Valley Fever Virus is now assigned to the Phenuiviridae family, genus Phlebovirus within Bunyaviroles. The information presented here directly pertains to viruses such as Rift Valley Fever Virus within the old family Bunyaviridae and that his how the terms "Bunyaviridae" and "Bunyavirus" will be used here. However, most of it also applies to the rest of the Bunyvirales order.

Bunyaviruses viruses are primarily arboviruses, in which the virus is transmitted by arthropod vectors to mammalian or avian hosts, and the arthropod vectors are infected when they take a blood meal on an infected animal to complete the transmission cycle. Bunyaviruses are enveloped viruses with negative-sense segmented single-stranded RNA genomes. The virions are generally spherical with diameters of around 90 to 100 nm. They have tripartite genomes (some viruses are bipartite) with large (L), medium (M), and small (S) RNA segments and a total genome size from about 10.5 to about 22.7 kps. The single-stranded RNA segments exist in a helical conformation within the virion complexed with the viral nucleocapsid protein (N), but exhibit pseudo-circular nature due to having complementary ends. The L and M segments are negative sense but the S and sometimes the M in some types of Bunyavirus may be ambisense (Elliott et al., 2014). The L segment normally encodes the viral enzymes including the RNA dependent RNA-polymerase and endonuclease, the M segment generally encodes the viral glycoproteins, which project from the viral surface and aid the virus in attaching to and entering the host cell, and the S segment encodes the nucleocapsid protein (Ariza et al., 2013).

Viral genome replication is catalyzed by the viral RNA dependent RNA-polymerase. The polymerase copies the negative polarity genome into a full-length positive polarity complementary RNA, and it then then converts the positive polarity RNA into a negative-polarity full-length RNA that is a new copy of the viral genome. Replication occurs in the cytoplasm of the host cell. As with all negative polarity RNA viruses, the viral RNA-dependent RNA polymerase does not recognize naked RNA, but rather a ribonucleoprotein complex. For the Bunyaviruses, this complex is comprised of the viral genomic RNAs and the viral N nucleocapsid protein.

Transcription of Bunyavirus RNAs also occurs in the cytoplasm, but instead of making full-length copies of the viral genome, it makes chimeric messenger RNAs (mRNA) that can be shorter than the negative polarity genomic template. These mRNAs contain a 5' cap that is derived from cellular mRNAs by a cleavage process called cap-snatching (Olschewski et al., 2020). The viral endonuclease activity within the L protein cleaves cellular mRNAs about 10-13 nt downstream of the cap, and then the L RNA-dependent RNA polymerase uses the capped oligonucleotide to prime RNA transcription and synthesizes the mRNAs (Amroun et al., 2017). The capped mRNAs are translated as usual for their mammalian host messages.

Viral replication is completed when the viral N protein binds to the genomic RNAs, and the ribonucleoprotein complexes are encapsidated into nascent virions. Virions are transmitted through the ER and Golgi apparatus, where they bud from the Golgi apparatus into vesicles which are transported to the cell surface and released by fusion with the cell membrane. Alternatively, some Bunyaviruses assemble directly at the plasma membrane and are released by budding through the membrane (Amroun et al., 2017).

Bunyaviruses primarily infect animals including humans, but some Bunyavirales within the genus Tospovirus can infect plants. The large majority of Bunyavirus infections are vector-borne arboviruses that are transmitted by the bite of arthropod, specifically a mosquito, tick, or fly. Therefore, arboviral Bunyavirus infections tend to increase as the incidence of the relevant vector increases in prominence. Certain genuses of Bunyavirus are known to cause in some incidents a non-specific flu like symptoms, but certain viruses are associated with a wide variety of specific human diseases.

1. Rift Valley Fever

The Rift Valley Fever virus is known to cause Rift Valley Fever in humans and a wide variety of animals, particularly livestock (Hartman, 2017). In humans, the virus can cause several symptoms. The majority of those infected with the Rift Valley Fever virus have either no symptoms or only a mild illness such as fever, headache, muscle pains, and liver abnormalities. In a small percentage of cases (<2%), the illness can progress to a hemorrhagic fever syndrome, meningoencephalitis (inflammation of the brain and tissues lining the brain), or serious eye complications. Typically, people recover within two to seven days after onset of symptoms. The proportion of humans who develop an infection is only about 1%. In livestock, the fatality level is significantly higher. In particular, pregnant livestock infected with Rift Valley Fever abort nearly 100% of fetuses. A wave of unexplained abortions typically signals the beginning of a epizootic. Other signs in livestock include vomiting and diarrhea, respiratory disease, fever, lethargy, anorexia and sudden death in young animals. There are no known treatment options for humans. There is a human vaccine but the vaccine is not widely available. Animals can be also be vaccinated against the disease.

2. Hantavirus Infections

Hantavirus infections are normally caused by exposure to the bodily excretions of rodents and primarily result in two different diseases in humans: hantavirus hemorrhagic fever with renal syndrome (HFRS) and hantavirus pulmonary syndrome (HPS). HFRS, while more common, is typically the milder of the two diseases.

HFRS is typically seen in Old World countries primarily in Asia and Europe. The disease is associated with little to no symptoms, often seen in Europe and called "nephropathia epidermica" to severe and potentially life threatening. The disease progression is often divided up into five phases. After an initial incubation period of 1-4 weeks, the HFRS typically starts with flu-like symptoms such as high fever, chills, headache, backache, blurred vision, abdominal pains, nausea, and vomiting, known as the febrile phase. While symptoms typically develop in 2-4 weeks, they make as long as 8 weeks to develop. Furthermore, some patients have been known to develop redness or inflammation of the eyes, flushing of the face, or a rash. Then the disease progresses to bleeding under the skin begins which is often paired with low blood pressure, and often patients exhibit tachycardia and hypoxemia, as blood platelets begin to drop. This phase is often followed by further internal bleeding throughout the body and may last 2 days. Then, during the oliguric phase, the patient develops renal failure, proteinuria, and other health issues. It is often in this phase which may last 3 to 7 days that death occurs. Finally, patients progress in the diuretic phase which is characterized by diuresis. Finally, the patient progresses into a convalescent phase as they begin to recover from the disease and symptoms improve. Even when not fatal, the disease may lead to permanent kidney damage. There is no known cure for HFRS.

On the other hand, HPS is typically seen in the New World with prominence in the United States and Canada. HPS has an initial incubation phase of 2-4 weeks, in which patients remain asymptomatic. After the incubation phase, patients then often experience 3-5 days of flu-like symptoms, including fever, cough, muscle pain, headache, lethargy, shortness of breath, nausca, vomiting and diarrhea. In the following 5-7 day the disease progresses into a cardiopulmonary phase where the patient's condition rapidly deteriorates into acute respiratory failure, characterized by the sudden onset of shortness of breath with rapidly evolving pulmonary edema, as well as cardiac failure, with hypotension, tachycardia and shock. In this phase, patients may develop acute respiratory distress syndrome that is often fatal despite mechanical ventilation and intervention with diuretics. After the cardiopulmonary phase, patients can enter a diuretic phase of 2-3 days characterized by symptom improvement and diuresis. The subsequent convalescence can last months to years after symptoms have started to improve. The death rate from HPS is 30% to 40%. There is no known treatment and currently only supportive therapies such as mechanical ventilation and supplemental oxygen are often used.

3. Crimean-Congo Hemorrhagic Fever

Crimean-Congo Hemorrhagic fever is a viral hemorrhagic fever that is transported by ticks primarily in Africa, the Balkans, the Middle Ease, and Asia. This disease often occurs in clusters and leads to death in from about 10% to about 40% of cases. The disease starts with a 1-3 days incubation period after a tick bite or 5-6 days after exposure to infected blood or other bodily fluids. The general onset of symptoms is often flu-like in nature including fever, body aches, muscle pain, headache, vomiting, and diarrhea. After 3-5 days, bleeding is typically seen and may include mood alterations, mental confusion, and throat petechiae. Soon, the patient will often exhibit nosebleeds, vomiting and black stools. In some severe cases, the liver becomes swollen and painful and may progress to liver failure. Additionally, other organ system may also begin to fail such as the kidneys and lungs or the patient may go into shock. Those who recover often begin to recover around 9-10 days after the first symptoms. There is no approved vaccine or treatment for Crimean-Congo hemorrhagic fever and the only treatments given are supportive in nature.

4. Encephalitis Bunyavirus Infections

Infections with Bunyaviruses are often associated with a variety of different encephalitis conditions including La Crosse encephalitis and California encephalitis. These conditions generally result in symptoms 3-15 days after a bite from an infected mosquito.

La Crosse encephalitis typically presents 5-15 days after infection as a general malaise with fever, nausea, headache, vomiting, and lethargy in most cases, but serious cases can result in seizures, coma, paralysis and permanent brain damage. The condition is generally mild with people under the age of 16, immunocompromised, or the elderly at the most risk from the virus.

California encephalitis generally has an incubation period of about 3-7 days with an early symptoms phases that last about 1-4 days that proceeds the encephalitis. These early symptoms include fever, chills, nausea, vomiting, headache, lethargy and abdominal pain. The encephalitis phase typically manifest fever, drowsiness, and lack of mental alertness and orientation with seizures occurring in 50% of children. Furthermore, 10% of patients advance to a comatose state. The total course of the disease generally last 10-14 days and some patients continue to exhibit ongoing seizures. The disease primarily afflicts children, but adults may act as carriers of the disease. While the disease is typically not fatal, 20% of patients can develop ongoing seizures and behavioral issues.

There is no known treatment for either condition and both are usually treated by management of the symptoms and eliminating potential sources of the mosquito vector.

B. CHEMICAL ENTITY

1. Chemical Genus and Species

The compounds of the present disclosure may be used to inhibit the replication of a bunyavirus. These compounds may be used in the treatment of infections with Rift Valley Fever virus, Crimean-Congo Hemorrhagic fever virus, La Crosse encephalitis virus, or various hantaviruses.

The compounds of the present disclosure are represented by the formula below:

(I)

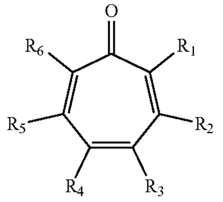

or (II)

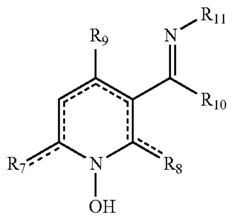

wherein the variables are defined herein.

TABLE 1

Non-limiting examples of compounds of the present disclosure.

| Compound ID | Structure |
|---|---|
| 46 | 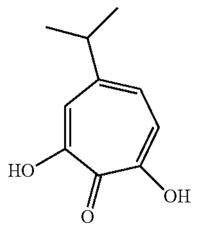 |
| 111 | 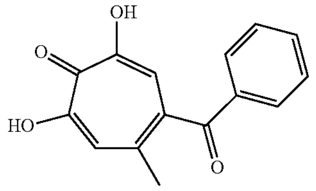 [SMILES: Cc1cc(O)c(=O)c(O)cc1C(=O)c1ccccc1] |
| 113 | 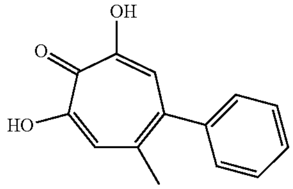 [SMILES: Cc1cc(O)c(=O)c(O)cc1-c1ccccc1] |
| 118 | 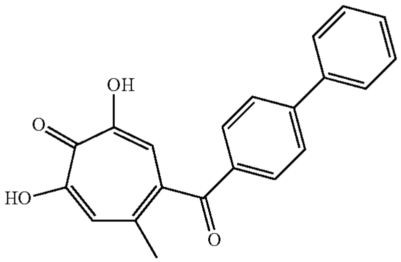 [SMILES: Cc1cc(O)c(=O)c(O)cc1C(=O)c1ccc(-c2ccccc2)cc1] |
| 120 | 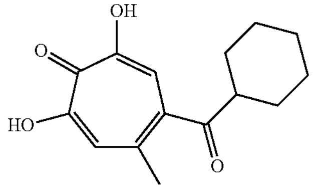 [SMILES: Cc1cc(O)c(=O)c(O)cc1C(=O)C1CCCCC1] |
| 196 | 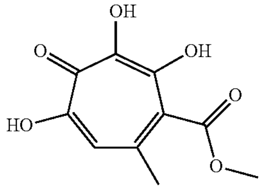 [SMILES: COC(=O)c1c(C)cc(O)c(=O)c(O)c1O] |
| 210 | 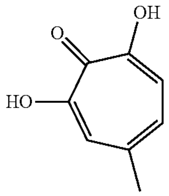 |

TABLE 1-continued
| Non-limiting examples of compounds of the present disclosure. | |
|---|---|
| Compound ID | Structure |
| 234 | 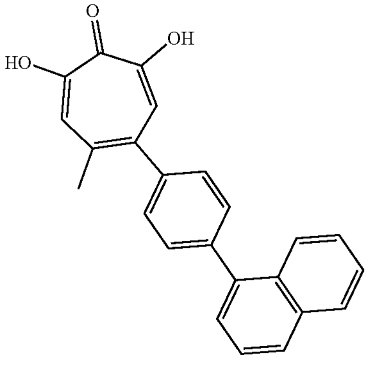 [SMILES: Cc1cc(O)c(=O)c(O)cc1-c1ccc(-c2cccc3ccccc23)cc1] |
| 260 | 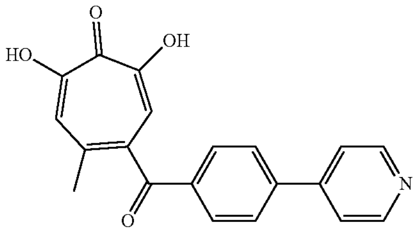 [SMILES: Cc1cc(O)c(=O)c(O)cc1C(=O)c1ccc(-c2ccncc2)cc1] |
| 265 | 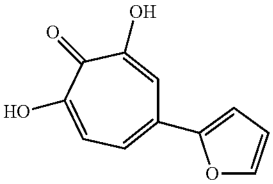 [SMILES: O=c1c(O)ccc(-c2ccco2)cc1O] |
| 308 | 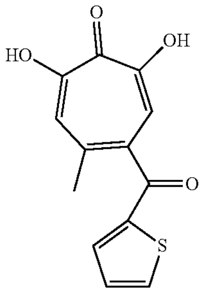 [SMILES: Cc1cc(O)c(=O)c(O)cc1C(=O)c1cccs1] |
| 311 | 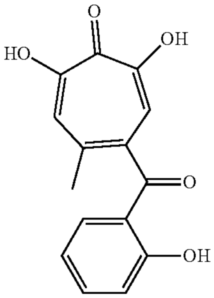 [SMILES: Cc1cc(O)c(=O)c(O)cc1C(=O)c1ccccc1O] |
TABLE 1-continued
| Non-limiting examples of compounds of the present disclosure. | |
|---|---|
| Compound ID | Structure |
| 320 | 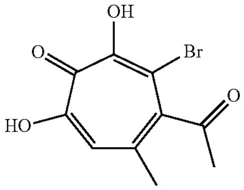 |
| 330 | 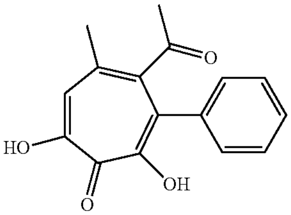 [SMILES: CC(=O)c1c(C)cc(O)c(=O)c(O)c1-c1ccccc1] |
| 331 | 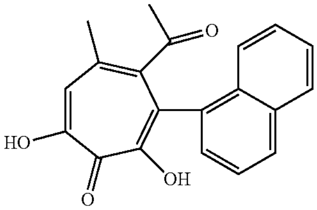 [SMILES: CC(=O)c1c(C)cc(O)c(=O)c(O)c1-c1cccc2ccccc12] |
| 335 | 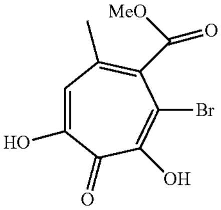 [SMILES: COC(=O)c1c(C)cc(O)c(=O)c(O)c1Br] |
| 336 | 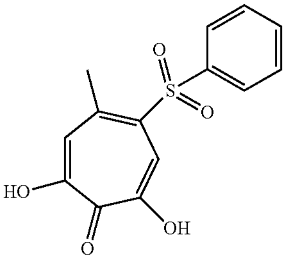 [SMILES: Cc1cc(O)c(=O)c(O)cc1S(=O)(=O)c1ccccc1] |
| 358 | 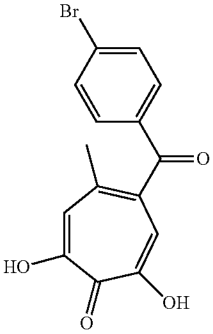 [SMILES: Cc1cc(O)c(=O)c(O)cc1C(=O)c1ccc(Br)cc1] |

TABLE 1-continued
Non-limiting examples of compounds of the present disclosure.
| Compound ID | Structure |
|---|---|
| 359 | 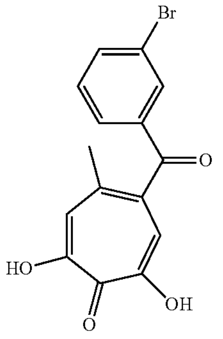 [SMILES: Cc1cc(O)c(=O)c(O)cc1C(=O)c1cccc(Br)c1] |
| 362 | 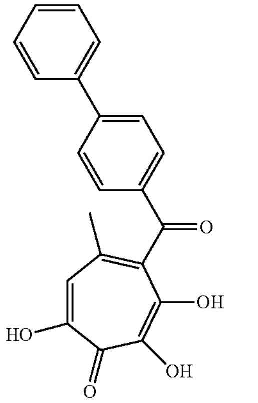 [SMILES: Cc1cc(O)c(=O)c(O)c(O)c1C(=O)c1ccc(-c2ccccc2)cc1] |
| 368 | 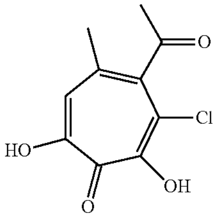 |
| 385 | 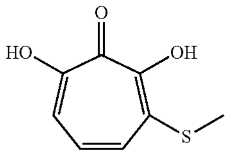 |
| 388 | 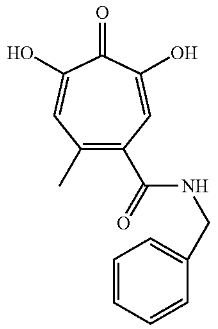 [SMILES: Cc1cc(O)c(=O)c(O)cc1C(=O)NCc1ccccc1] |
TABLE 1-continued
Non-limiting examples of compounds of the present disclosure.
| Compound ID | Structure |
|---|---|
| 389 | 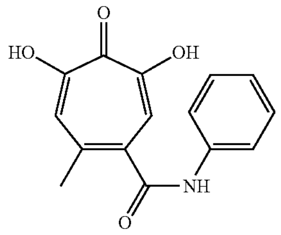 [SMILES: Cc1cc(O)c(=O)c(O)cc1C(=O)Nc1ccccc1] |
| 390 | 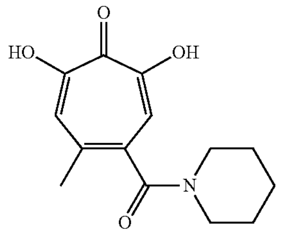 [SMILES: Cc1cc(O)c(=O)c(O)cc1C(=O)N1CCCCC1] |
| 539 | 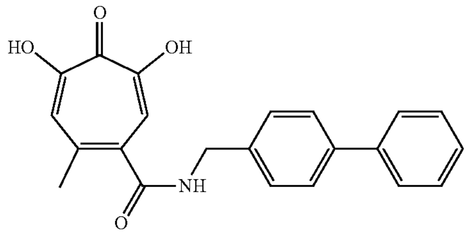 [SMILES: Cc1cc(O)c(=O)c(O)cc1C(=O)NCc1ccc(-c2ccccc2)cc1] |
| 694 | 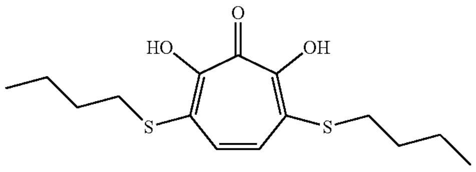 [SMILES: CCCCSc1ccc(SCCCC)c(O)c(=O)c1O] |
| 696 | 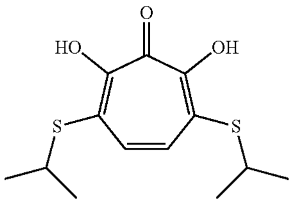 [SMILES: CC(C)Sc1ccc(SC(C)C)c(O)c(=O)c1O] |
| 809 | 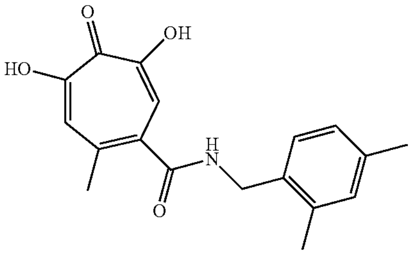 [SMILES: Cc1ccc(CNC(=O)c2cc(O)c(=O)c(O)cc2C)c(C)c1] |

TABLE 1-continued
Non-limiting examples of compounds of the present disclosure.
| Compound ID | Structure |
|---|---|
| 836 | 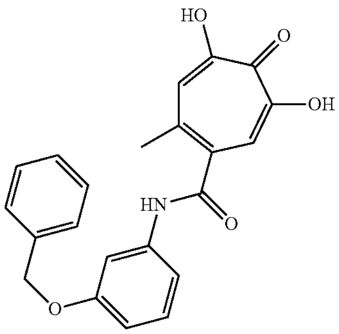 [SMILES: Cc1cc(O)c(=O)c(O)cc1C(=O)Nc1cccc(OCc2ccccc2)c1] |
| 838 | 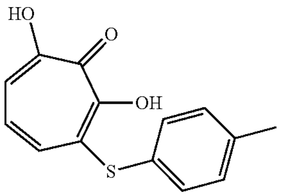 [SMILES: Cc1ccc(Sc2cccc(O)c(=O)c2O)cc1] |
| 840 | 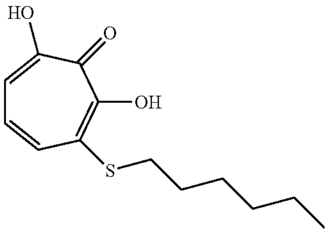 [SMILES: CCCCCCSc1cccc(O)c(=O)c1O] |
| 867 | 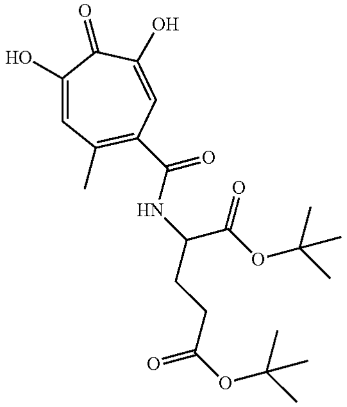 [SMILES: Cc1cc(O)c(=O)c(O)cc1C(=O)NC(CCC(=O)OC(C)(C)C)C(=O)OC(C)(C)C] |
TABLE 1-continued
Non-limiting examples of compounds of the present disclosure.
| Compound ID | Structure |
|---|---|
| 876 | 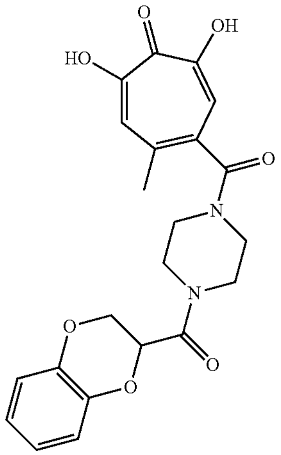 [SMILES: Cc1cc(O)c(=O)c(O)cc1C(=O)N1CCN(C(=O)C2COc3ccccc3O2)CC1] |
| 920 | 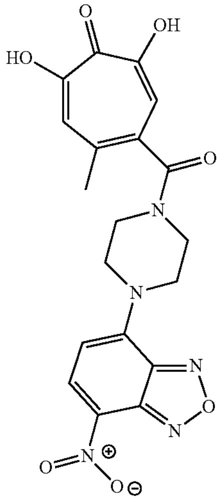 [SMILES: Cc1cc(O)c(=O)c(O)cc1C(=O)N1CCN(c2ccc([N+](=O)[O-])c3nonc23)CC1] |
| 1017 | 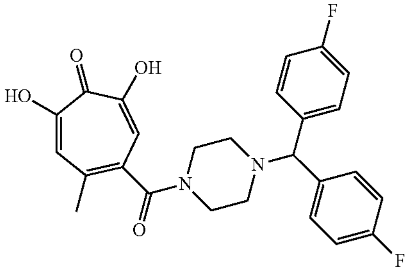 [SMILES: Cc1cc(O)c(=O)c(O)cc1C(=O)N1CCN(C(c2ccc(F)cc2)c2ccc(F)cc2)CC1] |
| 1019 | 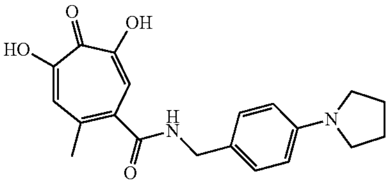 [SMILES: Cc1cc(O)c(=O)c(O)cc1C(=O)NCc1ccc(N2CCCC2)cc1] |

TABLE 1-continued
Non-limiting examples of compounds of the present disclosure.
| Compound ID | Structure |
| --- | --- |
| 1039 | 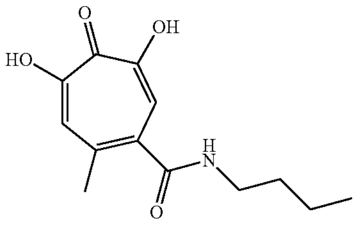 [SMILES: CCCCNC(=O)c1cc(O)c(=O)c(O)cc1C] |
| 208 | 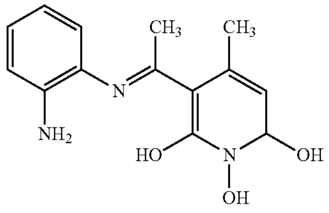 [SMILES: CC1=CC(O)N(O)C(O)=C1/C(C)=N/c1ccccc1N] |
| 515 | 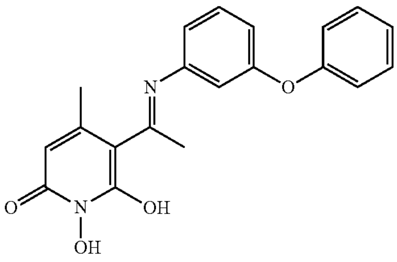 [SMILES: C/C(=N\c1cccc(Oc2ccccc2)c1)c1c(C)cc(=O)n(O)c1O] |
| 516 | 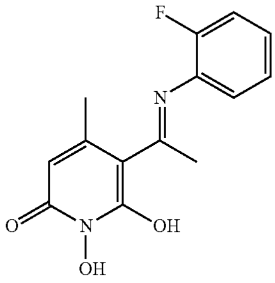 [SMILES: C/C(=N\c1ccccc1F)c1c(C)cc(=O)n(O)c1O] |
| 517 | 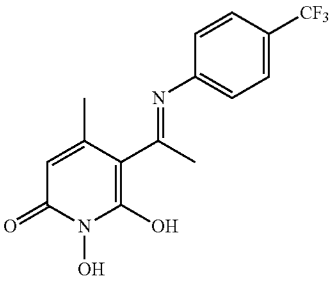 [SMILES: C/C(=N\c1ccc(C(F)(F)F)cc1)c1c(C)cc(=O)n(O)c1O] |
TABLE 1-continued
Non-limiting examples of compounds of the present disclosure.
| Compound ID | Structure |
| --- | --- |
| 668 | 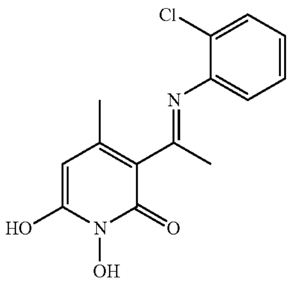 [SMILES: C/C(=N\c1ccccc1Cl)c1c(C)cc(O)n(O)c1=O] |
| 670 | 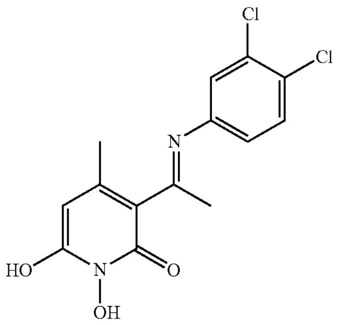 [SMILES: C/C(=N\c1ccc(Cl)c(Cl)c1)c1c(C)cc(O)n(O)c1=O] |
| 327 | 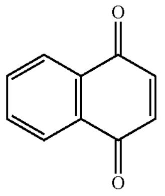 [SMILES: O=C1C=CC(=O)c2ccccc21] |
| 6 | 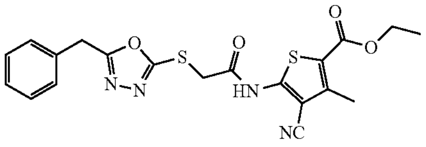 [SMILES: CCOC(=O)c1sc(NC(=O)CSc2nnc(Cc3ccccc3)o2)c(C#N)c1C] |
| 7 | 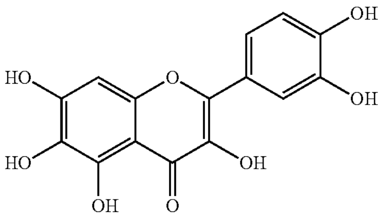 [SMILES: O=c1c(O)c(-c2ccc(O)c(O)c2)oc2cc(O)c(O)c(O)c12] |
| 8 | 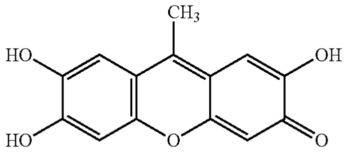 [SMILES: Cc1c2cc(O)c(=O)cc-2oc2cc(O)c(O)cc12] |
| 22 | 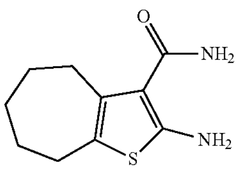 [SMILES: NC(=O)c1c(N)sc2c1CCCCC2] |

TABLE 1-continued

| Non-limiting examples of compounds of the present disclosure. | |
|---|---|
| Compound ID | Structure |
| 47 | 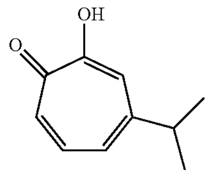 |
| 48 | 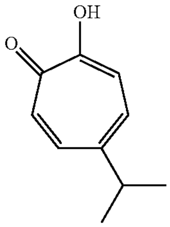 |
| 129 | 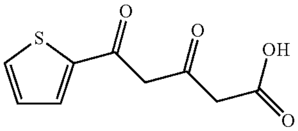 [SMILES: O=C(O)CC(=O)CC(=O)c1cccs1] |
| 138 | 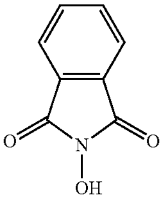 [SMILES: O=C1c2ccccc2C(=O)N1O] |
| 522 | 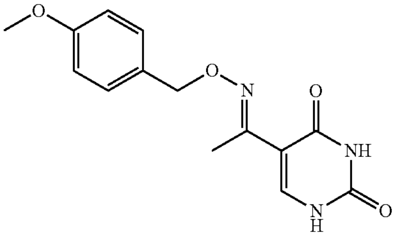 [SMILES: COc1ccc(CO/N=C(\C)c2c[nH]c(=O)[nH]c2=O)cc1] |
| 681 | 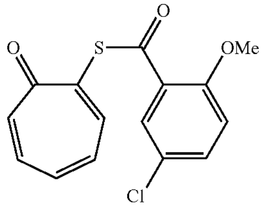 [SMILES: COc1ccc(Cl)cc1C(=O)Sc1cccccc1=O] |

The compounds of the present disclosure may be made using the methods outlined in the Examples section. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

Compounds of the disclosure may contain one or more asymmetrically-substituted carbon or nitrogen atoms and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration.

Chemical formulas used to represent compounds of the invention will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

Compounds of the disclosure may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the compounds of the present disclosure are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

Compounds of the present disclosure may also exist in prodrug form. Since prodrugs are known to enhance numerous desirable qualities of pharmaceuticals (e.g., solubility, bioavailability, manufacturing, etc.), the compounds employed in some methods of the disclosure may, if desired, be delivered in prodrug form. Thus, the disclosure contemplates prodrugs of compounds of the present disclosure as well as methods of delivering prodrugs. Prodrugs of the compounds employed in the disclosure may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It will be appreciated that many organic compounds can form complexes with solvents in which they are reacted or from which they are precipitated or crystallized. These complexes are known as "solvates." Where the solvent is water, the complex is known as a "hydrate." It will also be appreciated that many organic compounds can exist in more than one solid form, including crystalline and amorphous forms. All solid forms of the compounds provided herein, including any solvates thereof are within the scope of the present disclosure.

2. Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —$CO_2$H); "halo" means independently —F, —Cl, —Br or —I; "amino" means —$NH_2$; "hydroxyamino" means —NHOH; "nitro" means —$NO_2$; imino means =NH; "cyano" means —CN; "isocyanate" means —N=C=O; "azido" means —$N_3$; in a monovalent context "phosphate" means —OP(O)$(OH)_2$ or a deprotonated form thereof; in a divalent context "phosphate" means —OP(O)(OH)O— or a deprotonated form thereof; "mercapto" means —SH; and "thio" means =S; "sulfonyl" means —$S(O)_2$—; "hydroxylsulfonyl" means —$SO_2$OH; "aminosulfonyl" means —$SO_2NH_2$ and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "⩦" represents a single bond or a double bond. Thus, for example, the formula

includes

, , ,  and .

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "∿∿", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◀" means a single bond where the group attached to the thick end of the wedge is "out of the page." The symbol "⋯▮" means a single bond where the group attached to the thick end of the wedge is "into the page". The symbol "∿∿" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

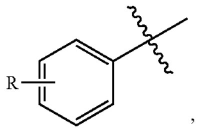, then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

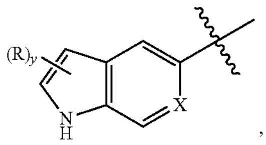, then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and compound classes below, the number of carbon atoms in the group is as indicated as follows: "Cn" defines the exact number (n) of carbon atoms in the group/class. "C≤n" defines the maximum number (n) of carbon atoms that can be in the group/class, with the minimum number as small as possible for the group in question, e.g., it is understood that the minimum number of carbon atoms in the group "alkenyl$_{(C\leq8)}$" or the class "alkene$_{(C\leq8)}$" is two. Compare with "alkoxy$_{(C\leq10)}$", which designates alkoxy groups having from 1 to 10 carbon atoms. Also compare "phosphine$_{(C\leq10)}$", which designates phosphine groups having from 0 to 10 carbon atoms. "Cn-n" defines both the minimum (n) and maximum number (n') of carbon atoms in the group. Thus, "alkyl$_{(C2-10)}$" designates those alkyl groups having from 2 to 10 carbon atoms. Typically the carbon number indicator follows the group it modifies, is enclosed with parentheses, and is written entirely in subscript; however, the indicator may also precede the group, or be written without parentheses, without signifying any change in meaning. Thus, the terms "C5 olefin", "C5-olefin", "olefin $_{(C5)}$", and "olefin$_{C5}$" are all synonymous. When any group or compound class below is used with the term "substituted", any carbon atoms of the chemical group replacing the hydrogen atom do not count towards the total carbon atom limit for that group or compound class. When any of the chemical groups or compound classes defined herein is modified by the term "substituted", any carbon atom in the moiety replacing the hydrogen atom is not counted. Thus methoxyhexyl, which has a total of seven carbon atoms, is an example of a substituted alkyl$_{(C1-6)}$. Unless specified otherwise, any chemical group or compound class listed in a claim set without a carbon atom limit has a carbon atom limit of less than or equal to twelve.

The term "saturated" when used to modify a compound or an atom means the compound or atom has no carbon-carbon double and no carbon-carbon triple bonds, except as noted below. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" signifies that the compound or chemical group so modified has a planar unsaturated ring of atoms with 4n+2 electrons in a fully conjugated cyclic π system. An aromatic compound or chemical group may be depicted as a single resonance structure; however, depiction of one resonance structure is taken to also refer to any other resonance structure. For example:

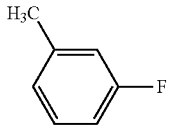

is also taken to refer to

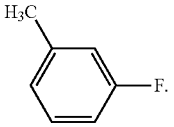

Aromatic compounds may also be depicted using a circle to represent the delocalized nature of the electrons in the fully conjugated cyclic π system, two non-limiting examples of which are shown below:

and

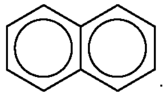

.

The term "alkyl" when used without the "substituted" modifier refers to a monovalent saturated aliphatic group with a carbon atom as the point of attachment, a linear or branched acyclic structure, and no atoms other than carbon and hydrogen. The groups $—CH_3$ (Me), $—CH_2CH_3$ (Et), $—CH_2CH_2CH_3$ (n-Pr or propyl), $CH(CH_3)_2$ (i-Pr, $^i$Pr or isopropyl), $—CH_2CH_2CH_2CH_3$ (n-Bu), $—CH(CH_3)CH_2CH_3$ (sec-butyl), $—CH_2CH(CH_3)_2$ (isobutyl), $—C(CH_3)_3$ (tert-butyl, t-butyl, t-Bu or $^t$Bu), and $—CH_2C(CH_3)_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups $—CH_2—$ (methylene), $CH_2CH_2—$, $—CH_2C(CH_3)_2CH_2—$, and $—CH_2CH_2CH_2—$ are non-limiting examples of alkanediyl groups. The term "alkylidene" when used without the "substituted" modifier refers to the divalent group $=CRR'$ in which R and R' are independently hydrogen or alkyl. Non-limiting examples of alkylidene groups include: $=CH_2$, $=CH(CH_2CH_3)$, and $=C(CH_3)_2$. An "alkane" refers to the compound H-R, wherein R is alkyl as this term is defined above. When these terms are used with the "substituted" modifier one or more hydrogen atom has been independently replaced by —OH, —F, —Cl, —Br, —I, $—NH_2$, $—NO_2$, $—N_2$, $—N_3$, $—CO_2H$, $—CO_2CH_3$, —CN, —SH, $—OCH_3$, $—OCH_2CH_3$, $—C(O)CH_3$, $—NHCH_3$, $—NHCH_2CH_3$, $—N(CH_3)_2$, $—C(O)NH_2$, $—C(O)NHCH_3$, $—C(O)N(CH_3)_2$, $—OC(O)CH_3$, $—NHC(O)CH_3$, $—S(O)_2OH$, $—S(O)_2NH_2$, or an amino protecting group. The following groups are non-limiting examples of substituted alkyl groups: $CH_2OH$, $—CH_2Cl$, $—CF_3$, $—CH_2CN$, $—CH_2C(O)OH$, $—CH_2C(O)OCH_3$, $—CH_2C(O)NH_2$, $—CH_2C(O)CH_3$, $—CH_2OCH_3$, $—CH_2OC(O)CH_3$, $—CH_2NH_2$, $—CH_2N(CH_3)_2$, and $—CH_2CH_2Cl$.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: $—CH(CH_2)_2$ (cyclopropyl), cyclobutyl, cyclopentyl, or cyclohexyl (Cy). The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

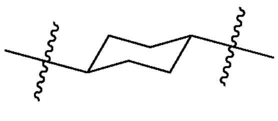 [SMILES: *C1CCC(*)CC1]

is a non-limiting example of cycloalkanediyl group. A "cycloalkane" refers to the compound H-R, wherein R is cycloalkyl as this term is defined above. When these terms are used with the "substituted" modifier one or more hydrogen atom has been independently replaced by —OH, —F, —Cl, —Br, —I, —$NH_2$, —$NO_2$, —$N_2$, —$N_3$, —$CO_2H$, —$CO_2CH_3$, —CN, —SH, —$OCH_3$, —$OCH_2CH_3$, —C(O)$CH_3$, —$NHCH_3$, —$NHCH_2CH_3$, —$N(CH_3)_2$, —C(O)$NH_2$, —C(O)$NHCH_3$, —C(O)$N(CH_3)_2$, —OC(O)$CH_3$, —NHC(O)$CH_3$, —$S(O)_2OH$, —$S(O)_2NH_2$, or an amino protecting group.

The term "alkenyl" refers to a monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH═$CH_2$ (vinyl), —CH═$CHCH_3$, —CH═$CHCH_2CH_3$, —$CH_2CH$═$CH_2$ (allyl), —$CH_2CH$═$CHCH_3$, and —CH═CHCH═$CH_2$. The term "alkenediyl" refers to a divalent unsaturated aliphatic group, with two carbon atoms as points of attachment, a linear or branched acyclic structure, at least one nonaromatic carbon-carbon double bond, no carbon-carbon triple bonds, and no atoms other than carbon and hydrogen. The groups —CH═CH—, —CH═C($CH_3$)$CH_2$—, —CH═$CHCH_2$—, and —$CH_2CH$═$CHCH_2$— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H-R, wherein R is alkenyl as this term is defined above. Similarly, the terms "terminal alkene" and "α-olefin" are synonymous and refer to an alkene having just one carbon-carbon double bond, wherein that bond is part of a vinyl group at an end of the molecule. When these terms are used with the "substituted" modifier one or more hydrogen atom has been independently replaced by —OH, —F, —Cl, —Br, —I, —$NH_2$, —$NO_2$, —$N_2$, —$N_3$, —$CO_2H$, —$CO_2CH_3$, —CN, —SH, —$OCH_3$, —$OCH_2CH_3$, —C(O)$CH_3$, —$NHCH_3$, —$NHCH_2CH_3$, —$N(CH_3)_2$, —C(O)$NH_2$, —C(O)$NHCH_3$, —C(O)$N(CH_3)_2$, —OC(O)$CH_3$, —NHC(O)$CH_3$, —$S(O)_2OH$, —$S(O)_2NH_2$, or an amino protecting group.

The term "alkynyl" refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡$CCH_3$, and —$CH_2C$≡$CCH_3$ are non-limiting examples of alkynyl groups. An "alkyne" refers to the class of compounds having the formula H-R, wherein R is alkynyl. When these terms are used with the "substituted" modifier one or more hydrogen atom has been independently replaced by —OH, —F, —Cl, —Br, —I, —$NH_2$, —$NO_2$, —$N_2$, —$N_3$, —$CO_2H$, —$CO_2CH_3$, —CN, —SH, —$OCH_3$, —$OCH_2CH_3$, —C(O)$CH_3$, —$NHCH_3$, —$NHCH_2CH_3$, —$N(CH_3)_2$, —C(O)$NH_2$, —C(O)$NHCH_3$, —C(O)$N(CH_3)_2$, —OC(O)$CH_3$, —NHC(O)$CH_3$, —$S(O)_2OH$, —$S(O)_2NH_2$, or an amino protecting group.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, $C_6H_4CH_2CH_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

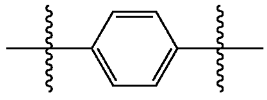
,
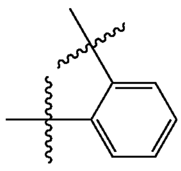
,
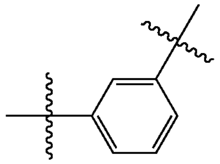
,
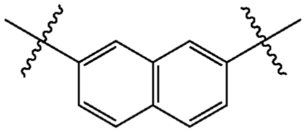

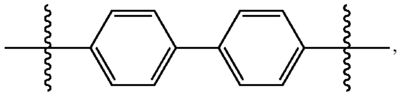
,
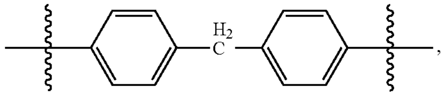
, and
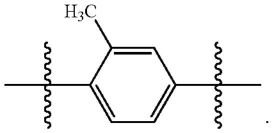
.

An "arene" refers to the compound H-R, wherein R is aryl as that term is defined above. Benzene and toluene are non-limiting examples of arenes. When these terms are used with the "substituted" modifier one or more hydrogen atom has been independently replaced by —OH, —F, —Cl, —Br, —I, —$NH_2$, —$NO_2$, —$N_2$, —$N_3$, $CO_2H$, —$CO_2CH_3$, —CN, —SH, —$OCH_3$, —$OCH_2CH_3$, —C(O)$CH_3$, —$NHCH_3$, —$NHCH_2CH_3$, —$N(CH_3)_2$, —C(O)$NH_2$, —C(O)$NHCH_3$, —C(O)$N(CH_3)_2$, —OC(O)$CH_3$, —NHC(O)$CH_3$, —$S(O)_2OH$, —$S(O)_2NH_2$, or an amino protecting group.

The term "aralkyl" refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. Furthermore, one or more of the sulfur atoms present in the group may be oxidized to the sulfonyl or sulfinyl state. If more than one ring is present, the rings may be fused or unfused in a pendent fashion. As used herein, the term does not preclude the presence of one or more alkyl, aryl, and/or aralkyl groups (carbon number limitation permitting) attached to the aromatic ring ring system. Non-limiting examples of heteroaryl groups include furanyl, imidazolyl, indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. The term "heteroarenediyl" refers to a divalent aromatic group, with two aromatic carbon atoms, two aromatic nitrogen atoms, or one aromatic carbon atom and one aromatic nitrogen atom as the two points of attachment, said atoms forming part of one or more aromatic ring structures, each with three to eight ring atoms, wherein at least one of the ring atoms of the aromatic ring structure(s) is nitrogen, oxygen or sulfur, and wherein the divalent group consists of no atoms other than carbon, hydrogen, aromatic nitrogen, aromatic oxygen and aromatic sulfur. If more than one ring is present, the rings are fused; however, the term heteroarenediyl does not preclude the presence of one or more alkyl or aryl groups (carbon number limitation permitting) attached to one or more ring atoms. Non-limiting examples of heteroarenediyl groups include:

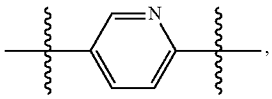,

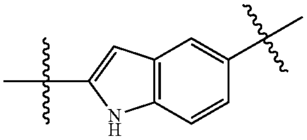

and

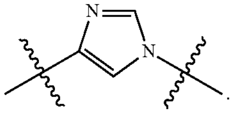.

A "heteroarene" refers to the compound H-R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, $—NH_2$, $—NO_2$, $—N_2$, $—N_3$, $—CO_2H$, $—CO_2CH_3$, —CN, —SH, $—OCH_3$, $—OCH_2CH_3$, $—C(O)CH_3$, $—NHCH_3$, $—NHCH_2CH_3$, $—N(CH_3)_2$, $—C(O)NH_2$, $—C(O)NHCH_3$, $—C(O)N(CH_3)_2$, $—OC(O)CH_3$, $—NHC(O)CH_3$, $—S(O)_2OH$, $—S(O)_2NH_2$, or an amino protecting group.

The term "heterocycloalkyl" refers to a monovalent non-aromatic group with a carbon atom or nitrogen atom as the point of attachment, said carbon atom or nitrogen atom forming part of one or more non-aromatic ring structures, each with three to eight ring atoms, wherein at least one of the ring atoms of the non-aromatic ring structure(s) is nitrogen, oxygen or sulfur, and wherein the heterocycloalkyl group consists of no atoms other than carbon, hydrogen, nitrogen, oxygen and sulfur. If more than one ring is present, the rings are fused. As used herein, the term does not preclude the presence of one or more alkyl groups (carbon number limitation permitting) attached to one or more ring atoms or an aromatic group fused to the heterocycloalkyl group. Also, the term does not preclude the presence of one or more double bonds in the ring or ring system, provided that the resulting group contains at least one non-aromatic ring system which is the point of attachment. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. N-pyrrolidinyl is an example of such a group. When these terms are used with the "substituted" modifier one or more hydrogen atom has been independently replaced by —OH, —F, —Cl, —Br, —I, $—NH_2$, $—NO_2$, $—N_2$, $—N_3$, $—CO_2H$, $—CO_2CH_3$, —CN, —SH, $—OCH_3$, $—OCH_2CH_3$, $—C(O)CH_3$, $—NHCH_3$, $—NHCH_2CH_3$, $—N(CH_3)_2$, $—C(O)NH_2$, $—C(O)NHCH_3$, $—C(O)N(CH_3)_2$, $—OC(O)CH_3$, $—NHC(O)CH_3$, $—S(O)_2OH$, $—S(O)_2NH_2$, or an amino protecting group.

The term "acyl" when used without the "substituted" modifier refers to the group —C(O)R, in which R is a hydrogen, alkyl, cycloalkyl, alkenyl, aryl, aralkyl, heteroaryl, or heterocycloalkyl, as those terms are defined above. The groups, CHO, $—C(O)CH_3$ (acetyl, Ac), $C(O)CH_2CH_3$, $—C(O)CH_2CH_2CH_3$, $—C(O)CH(CH_3)_2$, $—C(O)CH(CH_2)_2$, $—C(O)C_6H_5$, $—C(O)C_6H_4CH_3$, $—C(O)CH_2C_6H_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, $—NH_2$, $—NO_2$, $—N_2$, $—N_3$, $—CO_2H$, $—CO_2CH_3$, —CN, —SH, $—OCH_3$, $—OCH_2CH_3$, $—C(O)CH_3$, $—NHCH_3$, $—NHCH_2CH_3$, $—N(CH_3)_2$, $—C(O)NH_2$, $—C(O)NHCH_3$, $—C(O)N(CH_3)_2$, $—OC(O)CH_3$, $—NHC(O)CH_3$, $—S(O)_2OH$, $—S(O)_2NH_2$, or an amino protecting group. The groups, $—C(O)CH_2CF_3$, $—CO_2H$ (carboxyl), $—CO_2CH_3$ (methylcarboxyl), $—CO_2CH_2CH_3$, $—C(O)NH_2$ (carbamoyl), and $—CON(CH_3)_2$, are non-limiting examples of substituted acyl groups.

The term "alkoxy" when used without the "substituted" modifier refers to the group —OR, in which R is an alkyl, as that term is defined above. Non-limiting examples include: $—OCH_3$ (methoxy), $—OCH_2CH_3$ (ethoxy), $—OCH_2CH_2CH_3$, $—OCH(CH_3)_2$ (isopropoxy), $—OC(CH_3)_3$ (tert-butoxy), $—OCH(CH_2)_2$, —O-cyclopentyl, and —O-cyclohexyl. The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, $—NH_2$, $—NO_2$, $—N_2$, $—N_3$, $CO_2H$, $—CO_2CH_3$, —CN, —SH, $—OCH_3$, $—OCH_2CH_3$, $—C(O)CH_3$, $—NHCH_3$, $—NHCH_2CH_3$, $—N(CH_3)_2$, $—C(O)NH_2$, $—C(O)NHCH_3$, $—C(O)N(CH_3)_2$, $—OC(O)CH_3$, $—NHC(O)CH_3$, $—S(O)_2OH$, $—S(O)_2NH_2$, or an amino protecting group.

The terms "alkylsulfinyl", "alkylsulfinylamino", "alkylsulfonyl", and "alkylsulfonylamino" refers to the groups —S(O)R, —NHS(O)R, $—S(O)_2R$, and $—NHS(O)_2R$, respectively, in which R is an alkyl, as that term is defined above. The terms above may be used with any other appropriate chemical groups such as "cycloalkylsulfonyl", "alkenylsulfonyl", "alkynylsulfonyl", "arylsulfonyl", "aralkylsulfonyl", "heteroarylsulfonyl", and "heterocycloalkylsulfonyl" wherein R is a cycloalkyl, alkenyl, alkynyl, aryl, aralkyl, heteroaryl, or heterocycloalkyl group, as those terms are defined above.

An "amino acid" is a functional group which contains a $—CO_2H$ and a $—NH_2$ group on the same linear carbon skeleton. In its preferred embodiment, the term "amino acid" refers to one of the naturally occurring or commercially available amino acids as well as their enantiomers and diastereomers. As used herein, the term "amino acid residue" refers to a divalent amino acid which is linked through both the amine group and carboxylate group which are connected by an alkanediyl$_{(C\leq6)}$ which has been optionally substituted by —OH, —F, —Cl, —Br, —I, $—NH_2$, $—NO_2$, $CO_2H$, $—CO_2CH_3$, —CN, —SH, $—OCH_3$, $—OCH_2CH_3$, $—C(O)CH_3$, $—NHCH_3$, $—NHCH_2CH_3$, $—N(CH_3)_2$, $—C(O)NH_2$, $—OC(O)CH_3$, $—NHC(O)NH_2$, $—NHC(NH)NH_2$, or $—S(O)_2NH_2$ or an alkyl$_{(C1-12)}$, alkenyl$_{(C2-12)}$, alkynyl$_{(C2-12)}$, aryl$_{(C6-12)}$, aralkyl$_{(C7-12)}$, heteroaryl$_{(C1-12)}$, heterocycloalkyl$_{(C2-12)}$, acyl$_{(C1-12)}$, or a substituted version of any of these groups wherein one or more hydrogen atoms on the chemical group has been substituted with —OH, —F, —Cl, —Br, —I, $—NH_2$, $—NO_2$, $—CO_2H$, $—CO_2CH_3$, —CN, —SH, $—OCH_3$, $—OCH_2CH_3$, $—C(O)CH_3$, $—NHCH_3$, $—NHCH_2CH_3$, $—N(CH_3)_2$, $—C(O)NH_2$, $—OC(O)CH_3$, $—NHC(O)NH_2$, $—NHC(NH)NH_2$, or $—S(O)_2NH_2$, e.g.,

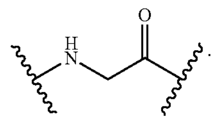 [SMILES: *NCC(*)=O]

In some embodiments, the amino acid residue is an α-amino acid wherein the alkanediyl is a methylene such that the carbonyl and the amine are joined by a single carbon. The amino acid residue may be one of the canonical amino acids such as leucine, isoleucine, tryptophan, cysteine, methionine, lysine, arginine, serine, threonine, tyrosine, phenylalanine, alanine, glycine, valine, glutamic acid, aspartic acid, asparagine, glutamine, proline, or histidine. These amino acid residues may be protected with one or more protecting groups on either the functional group on the side chain, the amine group, or the carboxylic acid group.

An "amino protecting group" is well understood in the art. An amino protecting group is a group which prevents the reactivity of the amine group during a reaction which modifies some other portion of the molecule and can be easily removed to generate the desired amine. Amino protecting groups can be found at least in Greene and Wuts, 1999, which is incorporated herein by reference. Some non-limiting examples of amino protecting groups include formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxycarbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, -4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Additionally, the "amino protecting group" can be a divalent protecting group such that both hydrogen atoms on a primary amine are replaced with a single protecting group. In such a situation the amino protecting group can be phthalimide (phth) or a substituted derivative thereof wherein the term "substituted" is as defined above. In some embodiments, the halogenated phthalimide derivative may be tetrachlorophthalimide (TCphth).

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects, or +/−5% of the stated value.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease. As used herein, the term "$IC_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living vertebrate organism, such as a human, monkey, cow, sheep, goat, dog, cat, mouse, rat, guinea pig, bird, fish or transgenic species thereof. In certain embodiments, the patient or subject is a primate. Non-limiting examples of human subjects are adults, juveniles, infants and fetuses.

As generally used herein, "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of the compound of the present disclosure which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this disclosure is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002).

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease, including reactivation.

"Prodrug" means a compound that is convertible in vivo metabolically into an inhibitor according to the present disclosure. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diasteromers can be resolved or separated using techniques known in the art. It is contemplated that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Effective amount," "therapeutically effective amount" or "pharmaceutically effective amount" means that amount which, when administered to a subject or patient for treating a disease, is sufficient to effect such treatment for the disease.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease. In some embodiments, treatment of a patient afflicted with one of the pathological conditions described herein comprises administering to such a patient an amount of compound described herein which is therapeutically effective in controlling the condition or in prolonging the survivability of the patient beyond that expected in the absence of such treatment. As used herein, the term "inhibition" of the condition also refers to slowing, interrupting, arresting or stopping the condition and does not necessarily indicate a total elimination of the condition. It is believed that prolonging the survivability of a patient, beyond being a significant advantageous effect in and of itself, also indicates that the condition is beneficially controlled to some extent.

The above definitions supersede any conflicting definition in any reference that is incorporated by reference herein. The fact that certain terms are defined, however, should not be considered as indicative that any term that is undefined is indefinite. Rather, all terms used are believed to describe the disclosure in terms such that one of ordinary skill can appreciate the scope and practice the present disclosure.

C. THERAPEUTIC METHODS

1. Pharmaceutical Formulations

In particular embodiments, where clinical application of an active ingredient is undertaken, it will be necessary to prepare a pharmaceutical composition appropriate for the intended application. Generally, this will entail preparing a pharmaceutical composition that is essentially free of pyrogens, as well as any other impurities or contaminants that could be harmful to humans or animals. One also will generally desire to employ appropriate buffers to render the complex stable and allow for uptake by target cells.

Aqueous compositions of the present disclosure comprise an effective amount of the active compound, as discussed above, further dispersed in pharmaceutically acceptable carrier or aqueous medium. Such compositions also are referred to as inocula. The phrase "pharmaceutically or pharmacologically acceptable" refers to compositions that do not produce an adverse, allergic or other untoward reaction when administered to an animal, or a human, as appropriate, as well as the requisite sterility for in vivo uses.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients also can be incorporated into the compositions.

Solutions of therapeutic compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

The therapeutic compositions of the present disclosure are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well-known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, a controlled release patch, salve or spray. In some embodiments, the topical formulation by used for administration to the skin, to mucosa membranes such as the eye, the eye lids, the genitals, the anus, or the inside of the mouth or nose, or in particular to the cornea.

An effective amount of the therapeutic composition is determined based on the intended goal. The term "unit dose" or "dosage" refers to physically discrete units suitable for use in a subject, each unit containing a predetermined quantity of the therapeutic composition calculated to produce the desired responses, discussed above, in association with its administration, i.e., the appropriate route and treatment regimen. The quantity to be administered, both according to number of treatments and unit dose, depends on the protection desired.

Precise amounts of the therapeutic composition also depend on the judgment of the practitioner and are peculiar to each individual. Factors affecting dose include physical and clinical state of the patient, the route of administration, the intended goal of treatment and the potency, stability and toxicity of the particular therapeutic substance.

2. Routes of Administration

Formulations of the present disclosure are suitable for oral administration. However, the therapeutic compositions of the present disclosure may be administered via any common route so long as the target tissue is available via that route. This includes ocular, nasal, buccal, corneal, rectal, vaginal, or topical administration, and intradermal, subcutaneous, intramuscular, intraperitoneal or intravenous injection. As such, compositions would be formulated pharmaceutically in route-acceptable compositions that include physiologically acceptable carriers, buffers or other excipients.

As with dosing amounts, the timing of delivery (including intervals and total number of doses) depends on the judgment of the practitioner and are peculiar to each individual. Factors affecting dose include physical and clinical state of the patient, the route of administration, the intended goal of treatment and the potency, stability and toxicity of the particular therapeutic substance.

3. Combination Therapy

In many clinical situations, it is advisable to use a combination of distinct therapies. Thus, it is envisioned that, in addition to the therapies described above, one would also wish to provide to the patient another clinically approved pharmaceutical therapies. Examples of standard therapies are described above. Combinations may be achieved by administering a single composition or pharmacological formulation that includes both agents, or with two distinct compositions or formulations, at the same time, wherein one composition includes the agents of the present disclosure and the other includes the standard therapy. Alternatively, standard therapy may precede or follow the present agent treatment by intervals ranging from minutes to weeks to months. In embodiments where the treatments are applied separately, one would generally ensure that a significant period of time did not expire between the time of each delivery, such that the agents would still be able to exert an advantageously combined effect on the subject. In such instances, it is contemplated that one would administer both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either the agent of the present disclosure, or the standard therapy will be desired. Various combinations may be employed, where the present disclosure compound is "A" and the standard therapy is "B," as exemplified below:

| | | | | | | | |
|---|---|---|---|---|---|---|---|
| A/B/A | B/A/B | B/B/A | A/A/B | B/A/A | A/B/B | B/B/B/A | B/B/A/B |
| A/A/B/B | A/B/A/B | A/B/B/A | B/B/A/A | B/A/B/A | B/A/A/B | B/B/B/A | |
| A/A/A/B | B/A/A/A | A/B/A/A | A/A/B/A | A/B/B/B | B/A/B/B | B/B/A/B | |

Other combinations are contemplated as well.

D. EXAMPLES

The following examples are included to further illustrate various aspects of the disclosure. It should be appreciated by those of skill in the art that the techniques disclosed in the examples which follow represent techniques and/or compositions discovered by the inventors to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

VI. Examples

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Inhibitors of Rift Valley Fever Virus

A. Methods

Compound synthesis. Thiotropolone (TTP) Compounds were synthesized as described in (Cao et al., 2018). Alpha-hydroxytropolone (αHT) compounds were synthesized as described in (Meck et al., 2012). For 265, 308, and 311 see (Donlin et al., 2017b). For 169 and 362 see (Hirsch et al., 2017). For 385, 694, 696, 698, 700, 702, 704, 703, 838, and 840 see (Agyemang et al., 2019). For 321, 336, 358, and 359 see (Lomonosova et al., 2017). For 388, 389, 390 and 539 see (Berkowitz et al., 2018). For 330 and 331 see (Donlin et al., 2017a). For 113, 118 and 120 see (Hirsch et al., 2014). For 260, see (Tavis et al., 2016). For 111 see (Meck et al., 2012). For 335 see: (Masaoka et al., 2016). 368 has not been previously reported.

N-hydroxypyridinedione (HPD) compounds not published previously include 513-518, 668, and 670. These compounds were synthesized following a three-step synthetic procedure (Scheme 1). The key structure 5-acetyl-1-(benzyloxy)-6-hydroxy-4-methylpyridin-2(1H)-one (ZEV1) was synthesized with an improved yield of 75% by refluxing a mixture of O-benzyl hydroxylamine (1 eq) and diketene (2 eq) in the presence of triethylamine (1 eq.) in dry toluene. Subsequently, the benzyl group was cleaved by catalytic hydrogenation over 10% palladium on carbon to afford the target compound ZEV2 almost quantitatively. 5-acetyl-1,6-dihydroxy-4-methylpyridin-2(1H)-one (ZEV2) was coupled with the appropriate substituted aniline using sulfuric acid as catalyst in absolute ethanol at reflux. The desired compounds were obtained in good yields ranging from 60% to 70%, with the only exception being 668 which was isolated in an overall yield of 25%.

Compounds were diluted to 10 mM in DMSO and stored in single-use aliquots in opaque tubes at −25° C.

Scheme 1. Synthesis of HPDs 513-518, 668, and 670. Reagents and conditions: (a) diketene, TEA, anh. toluene, 65° C., 4.5 h, Ar, yield: 75%; (b) $H_2$, Pd/C (10%), 40 psi, r.t, 20 min, yield: quantitative; (c) substituted aniline, conc. $H_2SO_4$, EtOH, 60° C., 4-24 h, Ar, yield 25-70%.

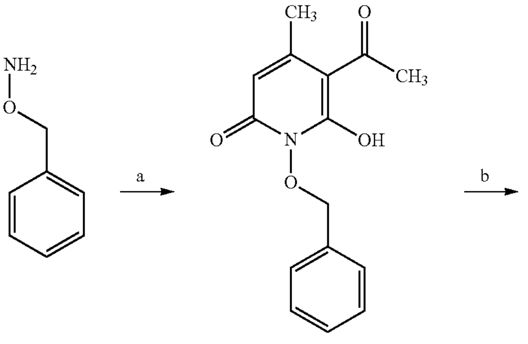

ZEV1

-continued

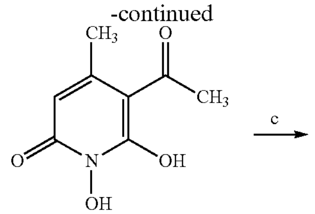

ZEV2

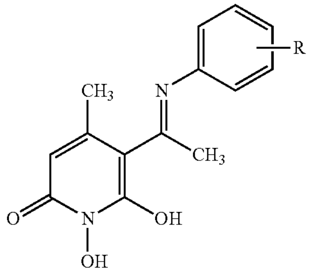

Primary screening. Vero cells, an African Green Monkey kidney cell line, were plated at $2\times10^5$ cells per mL in 96 well plates. Twenty-four hours later they were infected with RVFV strain MP12 at a multiplicity of infection of 0.005. Compound was added and the wells were overlayed with agarose to prevent long-range diffusion of the virus. After 26 hours plates were fixed, RVFV foci were stained using an anti-nucleocapsid protein antibody and colorimetric development reagent, and the number of viral foci were quantified using an automated ELISPOT machine (CTL universal S6) using the Immunospot software suite.

Efficacy against RVFV replication. 50% effective concentrations ($EC_{50}$) for key hits were determined by screening for suppression of RVFV growth using an 8 point, 2.5-fold dilution series of the compounds starting at 100 μM. The number of RVFV foci were quantified 1 day after infection using the focus formation assay employed for primary screening. $EC_{50}$ values were calculated by non-linear curve fitting in GraphPad Prism.

Cytotoxicity. Cytotoxicity for the compounds was estimated in Vero cells during the primary screening assays by staining the screening wells with crystal violet after RVFV foci had been counted and measuring cell monolayer density. Estimated 50% cytotoxic concentration ($CC_{50}$) values were derived by non-linear curve fitting in GraphPad Prism of the 4 data points derived from the primary screening plates.

Quantitative $CC_{50}$ values were measured in 2 systems. First, $CC_{50}$s were evaluated following 1 day of compound exposure in Vero cells by crystal violet staining of the multi-well plates used for $EC_{50}$ determination and measuring integrity of the cell monolayer. Second, cytotoxicity was measured in the HepG2-derived hepatoblastoma cell line HepDES19 (Guo et al., 2007). Cells were treated with a range of compound concentrations in a final DMSO concentration of 1% for 3 days and mitochondrial function was measured by MTS assays as described (Edwards et al., 2019a). $CC_{50}$ values were derived from the MTS and crystal violet staining data by non-linear curve fitting in GraphPad Prism.

RNaseH inhibition reactions. Activity of human ribonuclease H1 was measured using a FRET assay in which the RNA:DNA heteroduplex was formed by annealing a 18 nucleotide-long RNA oligonucleotide with a fluorescein label at the 3' end to a complementary DNA oligonucleotide with an Iowa Black quencher at the 5' end. Ribonuclease H (RNaseH) activity cleaves the RNA, permitting the fluorescein diffuse away from the quencher, increasing fluorescence. The oligonucleotides employed were:

```
DNA: 5'-IABkFQ-AGC TCC CAG GCT CAG ATC-3'
(IABkFQ: Iowa Black quencher)

RNA: 5'-GAU CUG AGC CUG GGA GCU FAM-3'
(FAM: Fluorescein fluorophore).
```

Recombinant human RNascH 1 was purified from *E. coli* as described in (Villa et al., 2016).

Enzyme and substrate (12.5 nM) were combined in 100 mM NaCl, 50 mM HEPES pH 8.0, 2 U RNase OUT (ThermoFisher), and test compound in a final concentration of 1% DMSO. Reactions were started by adding $MgCl_2$ to 5 mM and incubating at 37° C. for 90 min. with detection of fluorescence every 2 min. in a plate reader. The initial rate was determined for each compound concentration, and $IC_{50}$ values were determined from the reaction rates by non-linear curve fitting in GraphPad Prism.

Inhibition of *C. neoformans* growth. Compounds were tested in a limiting dilution assay w YNB-02 (0.67% yeast nitrogen base, 0.2% dextrose, pH 7.0 with 50 mM MOPS) plus 1% DMSO for 48 hours at 35° C. as described previously (Donlin et al., 2017b). Minimal 80% inhibitory concentration ($MIC_{80}$) values are the minimal concentration needed to inhibit 80% of *C. neoformans* growth relative to vehicle-treated controls.

Inhibition of *Staphylococcus* spp. and *Escherichia coli* growth. Inhibition of bacterial growth over 16-24 hours in Mueller-Hinton broth was done using the broth microdilution method (Clinical and Laboratory Standards Institute, 2015) as described previously (Cao et al., 2018). Inhibition was measured for some compounds against *S. saprophyticus* and others against *S. aureus*; little to no difference has observed in the inhibition profiles of these two bacterial species. Minimal 80% inhibitory concentration ($MIC_{80}$) values are reported as the minimal concentration needed to inhibit 80% of growth relative to mock-treated controls.

B. Results and Discussion

Primary screening. Primary screens were conducted that evaluated 397 compounds with known metal-chelating motifs or are similar to compounds with such motifs, most of which were assessed in 2 independent screens. The most common chemotype among the compounds screened was the troponoids (tropones, tropolones (TRP), thiotropolones (TTP), and α-hydroxytropolones (αHTs)), but the compound set also included a wide range of other chemotypes such as the N-hydroxypyridinediones (HPD), flavonoids, N-hydroxynapthyridinones, dihydronapthalenes (DHN), dioxobutanoic acids, hydroxyxanthanones, thienopyrimidinones, pyridinepiperazinthieonpyrimidins, N-biphenyltrihydroxybenzamides, and aminocyanothiophenes. Almost half of the compounds screened were αHTs as the library from which they were drawn was assembled in support of anti-Hepatitis B Virus ribonuclease H screens and the αHTs are a leading chemotype in that effort (Lomonosova et al., 2017; Lu et al., 2015; Li et al., 2020).

Cells were infected with RVFV, treated with 60, 20, 6.7, or 2.2 μM compound, and the number of RVFV foci were determined 24 hours later. Antiviral efficacy was calculated as an estimated 50% effective concentration ($EC_{50}$) from the number of RVFV foci detected. Following detection of the RVFV foci, cytotoxicity was estimated by qualitatively assessing monolayer integrity. In the later primary screening experiments, 50% cytotoxicity concentrations ($CC_{50}$s) were estimated by staining the cell monolayers with crystal violet and measuring the optical density of the stained cell monolayers. Screening hits were defined as compounds that i) had an estimated $EC_{50}$ determined from the 4-point screening assay of <20 μM and ii) had minimal evidence of cytotoxicity by either visual inspection of the cell monolayer or by measuring monolayer integrity. An example inhibition assay is in FIG. 1.

Figure 2:
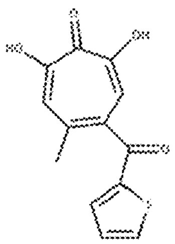
FIG. 2 shows structures of representative primary hit compounds.
Figure 2:
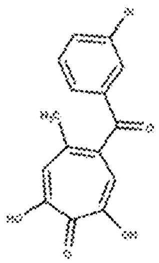
Figure 2:
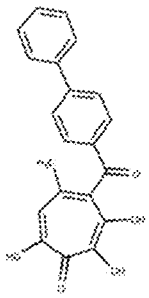
Figure 2:
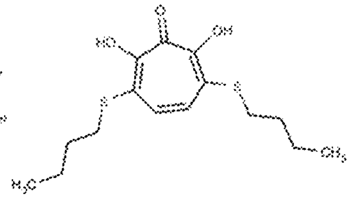
Figure 2:
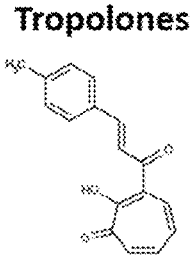
Figure 2:
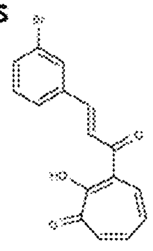
Figure 2:
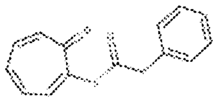
Figure 2:
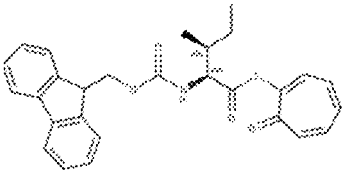
Figure 2:
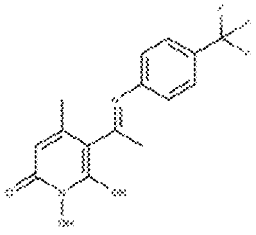
Figure 2:
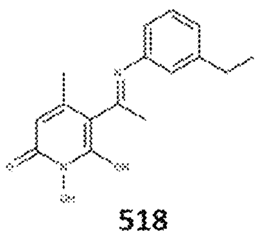
Figure 2:
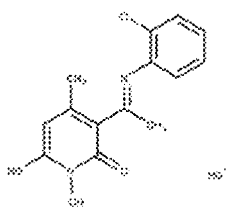
Figure 2:
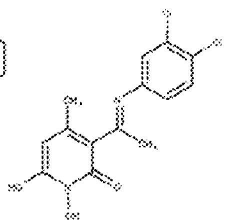
Figure 2:
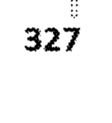

Forty-seven screening hits were identified (Table 2). Thirty-nine of 174 troponoids screened (22%) were hits, with 34 of them being αHTs, three being TRPs, and two being TTPs. In contrast, only eight of 223 non-troponoids (3.6%) were hits. Seven of these eight hits were HPDs. The hit rate among the 24 HPDs screened (29%) was similar to that among the αHTs. The remaining screening hit was a DHN. Structures of example hit compounds are FIG. 2.

TABLE 2

Primary screening hits against RVFV replication and select non-hits for comparison.

| Compound Number | Name [1] | Chemotype [2] | Estimated $EC_{50}$ (μM) | Estimated $CC_{50}$ (μM) | Preliminary η |
|---|---|---|---|---|---|
| | | α-Hydroxytropolones | | | |
| 390 | AB-2-70 | αHT | 0.1 | | |
| 308 | AG-11-18-P | αHT | 2 | 111 | 63 |
| 320 | NBA-1-13 | αHT | 2 | | |
| 330 | NBA-1-14 | αHT | 2 | | |
| 331 | NBA-1-31 | αHT | 2 | | |
| 335 | DH-2-60 | αHT | 3 | | |
| 336 | YA-1-78 | αHT | 3 | | |
| 311 | AG-11-3-P | αHT | 3 | 115 | 36 |
| 1017 | AL-23 | αHT | 3 | 120[3] | 40 |
| 359 | AG-11-108-C | TRP | 4 | | |
| 694 | NBA-1-127Bis | αHT | 6 | 120 | 21 |
| 362 | DS-1-69 | αHT | 6 | | |
| 1039 | AB-3-4S | αHT | 6 | 120 | 19 |
| 867 | DS-1-124 | αHT | 7 | 120 | 18 |
| 702 | NBA-1-159Mono | αHT | 7 | 120 | 17 |
| 210 | MoIMoII 19617 | αHT | 8 | 120 | 15 |
| 698 | NBA-1-150 | αHT | 8 | 120 | 15 |
| 838 | NBA-1-130 | αHT | 8 | 86 | 10 |
| 703 | NBA-1-159Bis | αHT | 9 | 120 | 14 |
| 539 | AB-2-91 | αHT | 10 | 71 | 7 |
| 696 | NBA-1-128Bis | αHT | 12 | 118 | 9 |
| 836 | RA-1-86 | αHT | 13 | 120 | 9 |
| 704 | NBA-1-160 | αHT | 14 | 120 | 9 |
| 840 | NBA-1-155-Mono | αHT | 14 | 120 | 9 |
| 389 | AB-2-66 | αHT | 16 | | |
| 711 | JS-116 | αHT | 17 | 120 | 7 |
| 710 | JS-112 | αHT | 17 | 120 | 7 |
| 809 | RA-1-82 | αHT | 17 | 64 | 4 |
| 799 | AIF-1.033 | αHT | 17 | 62 | 4 |
| 876 | JS-166 | αHT | 19 | 120 | 6 |
| 1019 | AL-22 | αHT | 19 | 120 | 6 |
| 388 | RA-1-30 | αHT | 19 | | |
| 234 | AB-1-51 | αHT | 19 | 120 | 6 |
| 920 | RA-1-104 | αHT | 19 | 120 | 6 |
| | | Thiotropolones | | | |
| 680 | BE1105 | TTP | 0.3 | 0.9 | 3 |
| 686 | BE1111 | YTP | 2 | 120 | 56 |
| | | Tropolones | | | |
| 341 | Specs AP-355/40802214 | TRP | 2 | | |
| 342 | Specs AP-355/40633885 | TRP | 2 | | |
| 340 | Specs AP-355/40633884 | TRP | 3 | | |
| | | Dihydronapthalene | | | |
| 327 | Aldrich Select CNC_ID 444085867 | DHN | 2 | | |
| | | N-Hydroxypyridinediones | | | |
| 518 | ZEV-V3 | HPD | 7 | 120 | 17 |
| 670 | ZEV-V7 | HPD | 10 | 120 | 12 |
| 668 | ZEV-V5 | HPD | 11 | 120 | 11 |
| 517 | ZEV-V2 | HPD | 13 | 120 | 9 |
| 208 | Sun B8155 | HPD | 14 | 120 | 9 |
| 515 | ZEV-E2 | HPD | 14 | 120 | 9 |
| 516 | ZEV-V1 | HPD | 19 | 120 | 6 |
| | | Example inactive compounds | | | |
| 6 | Chembridge 7929959 | ACT | 120 | | |
| 7 | Quercetagetin | FLV | 120 | | |

TABLE 2-continued

Primary screening hits against RVFV replication and select non-hits for comparison.

| Compound Number | Name [1] | Chemotype [2] | Estimated $EC_{50}$ (μM) | Estimated $CC_{50}$ (μM) | Preliminary η |
|---|---|---|---|---|---|
| 8 | Sigma S439274 | HXT | 120 | | |
| 22 | Sigma n8164 | TPD | 120 | | |
| 47 | β-thujaplicin | TRP | 120 | | |
| 48 | γ-thujaplicin | TRP | 120 | | |
| 129 | Aldrichselect CNC_ID 249465147 | DOB | 120 | | |
| 138 | Sigma HS3704 | HPD-like | 120 | | |
| 522 | ZAU5 | HPD-like | 120 | 1 | <1 |
| 681 | BE1106 | TTP | 120 | 2 | <2 |
| 700 | NBA-1-157Bis | αHT | 120 | 120 | >1 |
| 712 | IS-108 | αHT | 120 | 20 | <2 |

[1] Chemist's name for the compound, common name, or vendor catalog number.
[2] αHT, α-Hydroxytropolone; TRP, tropolone; TTP, thiotropolone; DHN, dihydronapthalene; HPD, N-Hydroxypyridinedione; FLV, flavenoid; DOB, dioxobutanoic acid; HXT, hydroxyxanthanone; TPD, thieopyrimidinone; ACT, aminocyanothiophene.
[3]Values of 120 indicate the data were at or above the upper limit of quantification in the assay.

Efficacy. $EC_{50}$ values were determined for the 36 compounds with an estimated $EC_{50}$ in the primary screen of ≤14 μM, plus 12 additional compounds selected to broaden the chemical diversity assessed and to spot-check compounds with poorer estimated $EC_{50}$s. Cells were treated with a range of compound concentrations, the number of RVFV foci were counted under each condition, and $EC_{50}$s were calculated by non-linear curve fitting. $EC_{50}$s ranged from 0.54 to >120 μM (Table 3).

TABLE 3

$EC_{50}$s against RVFV replication.

| | | | | | | | | Counter screens | | | |
|---|---|---|---|---|---|---|---|---|---|---|---|
| Compound number | Compound name | Chemotype | RVFV ($EC_{50}$, μM) | $CC_{50}$ Vero (μM) | $CC_{50}$ HepDES19 (μM) | TI Vero | TI HepDES19 | Human RNaseH1 ($IC_{50}$, μM) | *Staphylococcus* spp. ($MIC_{80}$, μM) | *E. coli* ($MIC_{80}$, μM) | *C. neoformans* ($MIC_{80}$, μM) |
| 46 | β-thujaplicinol | αHT | 13.8 | 250* | 25.0 | 18.1 | 1.8 | 58 | 20 | 44 | 8.0 |
| 111 | CM1012-6f | αHT | 19.0 | 250* | 35.5 | 13.2 | 1.9 | 48 | — | — | 36 |
| 113 | RM-YM-1-0613 | αHT | 10.3 | 250* | 47.0 | 24.3 | 4.6 | 174 | — | — | 24 |
| 118 | RM-MD-2-0813 | αHT | 11.0 | 248 | 17.0 | 22.5 | 1.5 | 500* | — | — | 15 |
| 120 | RM-MD-1-0713 | αHT | 15.6 | 250* | 42.4 | 16.0 | 2.7 | 81 | — | — | 12 |
| 196 | DH-3-37 | αHT | 23.9 | 250* | 6.0 | 10.5 | 0.3 | 408 | 67 | — | |
| 208 | Sun B8155 | HPD | 120* | 250* | 14.4 | <1.0 | <1.0 | 194 | — | — | 30 |
| 210 | MolMoll 19617 | αHT | 14.6 | 283 | 71.0 | 19.4 | 4.9 | 85 | — | — | 15 |
| 260 | AG-I-84-P | αHT | 31.6 | 250* | 45.0 | 7.9 | 1.4 | 277 | — | — | 50 |
| 265 | AG58 | αHT | 15.4 | 250* | 25.5 | 16.2 | 1.7 | 57 | 30 | — | 11 |
| 308 | AG-II-18-P | αHT | 0.54 | 217 | 25.8 | 402 | 47.8 | 46 | 44 | 25 | 11 |
| 311 | AG-II-3-P | αHT | 11.6 | 250* | 31.7 | 21.6 | 2.7 | 26 | 67 | 30 | 15 |
| 320 | NBA-I-13 | αHT | 20.1 | 120* | 49.5 | 6.0 | 2.5 | 37 | — | — | 49 |
| 327 | Aldrich Select CNC_ID 444085867 | DHN | 39.7 | 42.9 | 18.5 | 1.1 | 0.5 | 47 | — | — | 9.1 |
| 330 | NBA-I-14 | αHT | 9.5 | 300* | 56.2 | 31.6 | 5.9 | 476 | 44 | — | 4.0 |
| 331 | NBA-I-31 | αHT | 15.8 | 80.4 | 36.6 | 5.1 | 2.3 | 448 | 67 | — | 11 |
| 335 | DH-2-60 | αHT | 40.8 | 120* | 78.0 | 2.9 | 6.0 | 111 | — | — | 50 |
| 336 | YA-I-78 | αHT | 9.0 | 65.8 | 45.4 | 7.3 | 5.0 | 85 | — | — | 50 |
| 340 | Specs AP-355/40633884 | TRP | 27.3 | 70.0 | 18.7 | 2.6 | 0.7 | 500* | — | — | 49 |

TABLE 3-continued

| Compound number | Compound name | Chemotype | RVFV ($EC_{50}$, μM) | $CC_{50}$ Vero (μM) | $CC_{50}$ HepDES19 (μM) | TI Vero | TI HepDES19 | Counter screens: Human RNaseH1 ($IC_{50}$, μM) | Counter screens: *Staphylococcus* spp. ($MIC_{80}$, μM) | Counter screens: *E. coli* ($MIC_{80}$, μM) | Counter screens: *C. neoformans* ($MIC_{80}$, μM) |
|---|---|---|---|---|---|---|---|---|---|---|---|
| $EC_{50}$s against RVFV replication. | | | | | | | | | | | |
| 341 | Specs AP-355/ 40802214 | TRP | 25.2 | 300* | 17.1 | 11.9 | 0.7 | 500* | 44 | — | 24 |
| 342 | Specs AP-355/ 40633885 | TRP | 55.5 | 300* | 30.4 | 5.4 | 0.5 | 500* | — | — | 24 |
| 358 | AG-II-83-P | αHT | 9.0 | 250* | 12.5 | 27.8 | 1.4 | 43 | | 20 | 11 |
| 359 | AG-II-108-C | αHT | 5.1 | 170 | 19.4 | 33.3 | 3.8 | 65 | — | — | 24 |
| 362 | DS-I-69 | αHT | 2.6 | 77.8 | 5.4 | 29.9 | 2.1 | 212 | | — | 24 |
| 368 | NBA-I-82 | αHT | 25.4 | 250* | 31.0 | 9.8 | 1.2 | 115 | — | — | 24 |
| 385 | NBA-I-116A | αHT | 25.2 | 250* | 100* | 9.9 | 4.0 | 176 | — | — | 24 |
| 388 | RA-1-30 | αHT | 9.0 | 239 | 19.8 | 26.6 | 2.2 | 166 | 67 | 67 | 11 |
| 389 | AB-2-66 | αHT | 8.8 | 250* | 26.5 | 28.4 | 3.0 | 309 | 44 | 44 | 3.5 |
| 390 | AB-2-70 | αHT | 11.9 | 250* | 29.8 | 21 | 2.5 | 106 | — | — | 11 |
| 515 | ZEV-E2 | HPD | 24.3 | 120* | 71.3 | 4.9 | 2.9 | 622 | — | — | 11 |
| 517 | ZEV-V2 | HPD | 120* | 120* | 91.0 | 1.0 | <1.0 | 135 | — | — | 24 |
| 518 | ZEV-V3 | HPD | 20.0 | 120* | 91.4 | 6.0 | 4.6 | 436 | 67 | — | 24 |
| 539 | AB-2-91 | αHT | 18.6 | 300* | 3.6 | 16.1 | <1.0 | 105 | 38 | — | 4.5 |
| 668 | ZEV-V5 | HPD | 19.2 | 120* | 76.8 | 6.2 | 4.0 | 165 | — | — | |
| 670 | ZEV-V7 | HPD | 14 | 120* | 69.0 | 8.6 | 4.9 | 356 | — | — | 69 |
| 680 | BE1105 | TTP | 120* | 120* | 95.6 | 1.0 | <1.0 | 652 | 13 | 30 | 0.40 |
| 686 | BE1111 | TTP | 120* | 120* | 42.6 | 1.0 | <1.0 | 500* | 30 | — | 0.85 |
| 694 | NBA-I-127 Bis | αHT | 3.7 | 22.1 | 1.8 | 6.0 | <1.0 | 500* | 9 | — | 2.3 |
| 696 | NBA-I-128 Bis | αHT | 6.0 | 56.5 | 14.1 | 9.4 | 2.4 | 500* | 13 | 20 | 1.5 |
| 698 | NBA-I-150 | αHT | 11.7 | 42.9 | 13.7 | 3.7 | 1.2 | 261 | 20 | 44 | 38 |
| 702 | NBA-I-159 Mono | αHT | 8.8 | 35.6 | 17.4 | 4.0 | 2.0 | 34 | 13 | 9 | 0.55 |
| 703 | NBA-I-159 Bis | αHT | 16.1 | 53.2 | 8.2 | 3.3 | <1.0 | 61 | 13 | — | 7.0 |
| 704 | NBA-I-160 | αHT | 14.3 | >120 | 21.6 | 8.4 | 1.5 | 25 | 20 | — | 1.8 |
| 838 | NBA-I-130 | αHT | 12.7 | 300* | 18.6 | 23.6 | 1.5 | 100 | — | — | 1.0 |
| 840 | NBA-I-155-Mono | αHT | 31.6 | 120* | 21.5 | 3.8 | <1.0 | 73 | — | — | 1.0 |
| 867 | DS-1-124 | αHT | 8.7 | 120* | 5.2 | 13.8 | <1.0 | 500* | — | — | 9.0 |
| 1017 | AL-23 | αHT | 8.0 | 54.7 | 3.9 | 6.8 | <1.0 | 30 | — | — | 6.0 |
| 1039 | AB-3-45 | αHT | 8.9 | 120* | 8.7 | 13.5 | <1.0 | 209 | — | — | 12 |

Cytotoxicity and therapeutic indexes. Cytotoxicity was quantitatively evaluated in two manners for the compounds evaluated in $EC_{50}$ assays. First, $CC_{50}$ values after one day of compound exposure in Vero cells were calculated by staining the plates of cells used for the $EC_{50}$ assays with crystal violet and measuring cell monolayer integrity. This permitted measurement of cytotoxicity in the same culture wells as were used for efficacy assays. Second, cytotoxicity was assessed in the HepG2 hepatoblastoma cell line derivative HepDES19 (Guo et al., 2007) to model longer-duration compound exposure in the liver cells. Cells were treated with a range of compound concentrations for three days and mitochondrial function was measured using MTS assays. $CC_{50}$ values ranged from 22 to >250 μM in Vero cells and 1.8 to >100 μM in the hepatoblastoma cells (Table 3).

Therapeutic indexes ($CC_{50}/EC_{50}$) were calculated for all compounds with $EC_{50}$ values based on cytotoxicity in both Vero cells after one day compound treatment and in HeDES19 cells after three days of treatment. TIs ranged from <1 to 402 in Vero cells and <1 to 48 in HepDES19 cells (Table 3). Confirmed hits were defined as compounds with TIs>5 in Vero cells (n=36) because this indicates that the reduction in RVFV foci was not a result of non-specific killing of the Vero cells in which the screening was done. Structures of all compounds in Tables 2 and 3 and structures of all confirmed hit compounds are in Table 1.

Selectivity. αHTs and N-hydroxyisoquinolinediones that are closely related to the HPDs work against HIV by chelating the Mg++ ions in the viral integrase and/or ribonuclease H enzyme active sites (Himmel et al., 2009; Suchaud et al., 2012; Wang et al., 2018). The TRP and TPP compounds may work in a similar manner, but they likely target mono-metalloenzymes rather than di-metalloenzymes because they have only two chelating motifs rather than the three found in the αHTs and HPDs. Mono- and di-metalloenzymes are common, so specificity for RVFV was assessed for the compounds for which $EC_{50}$ values were measured. Their biochemical activity was first evaluated against recombinant human ribonuclease H1, a dimetallo-$Mg^{++}$-dependent endonuclease that is sensitive to some of these compound classes. 50% inhibitory concentrations ($IC_{50}$) were determined for the compounds in Table 3 by measuring the rate of cleavage of the RNA strand in a short RNA:DNA heteroduplex substrate in the presence of the compounds. $IC_{50}$s against RNase H1 ranged from 25 to >500 μM (Table 3), implying a wide selectivity index for RVFV inhibition compared to off-target suppression of RNase H1H1.

Metal chelating compounds, particularly the troponoids, can have broad anti-microbial activity (Meck et al., 2014), so efficacy of the RVFV hit compounds for which $EC_{50}$ values were obtained against three other human pathogens: the fungus *Cryptococcus neoformans* and the bacteria *Staphylococcus* spp., and *E. coli* (Table 3). These compounds had little efficacy against the Gram-negative bacterium *E. coli*, with only 10 of the 48 compounds assessed in the counter-screens being active and the best 80% minimum inhibitory concentration ($MIC_{80}$) value being 9 μM. Antibiotic activity was observed more frequently for the Gram-positive bacteria *S. aureus* and *S. saprophyticus*, with 20 having measurable $MIC_{80}$s that ranged from 9-67 μM. The compounds as a set were modestly active against *C. neoformans*, with 39 having $MIC_{80}$s≤25 μM (range 0.55-69 μM). Overall, these primary screening hits against RVFV have some cross-reactivity with other microbes, but the significance of this cross-inhibition cannot be determined until on the mechanism(s) of action for these compounds is identified.

Efficacy and cytotoxicity. Most primary hit compounds were either αHTs or HPDs, but TRP, TTP, and DHN hits were also found. This distribution of hit compounds is partially duc sampling bias based on the disproportionate proportion of αHTs and HPDs in the compound collection screened, but sampling bias does not fully explain the hit distribution because there were many chemotypes in the compound collection where hits were not found, including dioxobutanoic acids, hydroxyxanthanones, thienopyrimidinones, pyridinepiperazinthieonpyrimidins, N-biphenyltrihydroxybenzamides, and aminocyanothiophenes. $EC_{50}$ values of the 48 compounds for which quantitative data were obtained ranged from 0.54 to >120 μM (Table 3). Therapeutic indexes for these compounds in Vero cells in which the screening was conducted range from 1 to 402 (average=21). Thirty-six compounds were confirmed hits (TIs>5 in Vero cells, 9.1% of the compounds screened) that indicating that they were due to bona fide inhibition of RVFV rather than secondary effects of cytotoxicity. However, the much lower TI values in the three-day assays in HepDES19 cells (<1 to 48) indicate that compounds active versus RVFV replication can have substantial cytotoxicity in human liver-derived cells that must be addressed during subsequent hit-to-lead medicinal chemistry campaigns. One avenue for reducing cytotoxicity, at least for the αHTs, may be to reduce the lipophilicity and number of aromatic rings in the molecules because these parameters correlate with αHT toxicity (Lomonosova et al., 2017). RVFV infections proceed rapidly in vivo, so optimizing these hits to achieve toxicity profiles suitable for a one- to two-week treatment regimen in RVFV-infected patients or animals will likely be enough to yield usable drugs.

Selectivity. Identification of primary screen hits among the αHT, HPD, TRP, TTP, and DHN chemotypes indicates that a range of compounds can inhibit RVFV replication, but the lack of hits among the other chemotypes screened implies that there is specificity to RVFV inhibition. The potential for specific inhibition of RVFV was confirmed by the wide range of inhibition patterns observed during counter-screening (Table 3). For example, 362 had an $EC_{50}$ of 2.6 μM vs. RVFV, an $IC_{50}$ against human ribonuclease H1 of 212 μM, was inactive against *E. coli* growth, and was modestly effective against *C. neoformans* ($MIC_{80}$=24 μM). In contrast, 260 was poorly active or inactive in all of the counter-screens, and 389 had good to moderate activity against all microbes screened but was nearly inactive against human RNase H1. This indicates that although that these chemotypes can have broad anti-microbial activity, individual compounds can be selective through specific interactions with their spectrum of potential targets.

Structure-activity relationships. The 174 troponoids (αHTs, TRPs, TTPs) evaluated yielded 33 confirmed hits with TI values >5 (Table 3). Inhibition of RFVF by tropolones appears to be dependent by a 3-points of contact with the target molecule. For example, while the tropolone natural products β- and Y-thujaplicin were inactive against the at concentrations upwards of 100 μM, the αHT natural product β-thujaplicinol was active against the virus, with an $EC_{50}$ of 13.8 μM. These trends extended to synthetic αHTs, of which 13 different molecules had $EC_{50}$ values under 10 μM, the most potent of which had an $EC_{50}$ of 0.54 μM (308). These more potent molecules had a broad range of appendages, such as ketone (308, 362, 359, 358, 330), amides (1017, 867, 388, 389, 1039), thioether (694, 696, 702), sulfoxide (336) and aryl (330), and also included a 3,7-dihydroxytropolone (362), demonstrating tolerance to a variety of functional groups. Apart from the αHTs, three additional tropolones had measurable $EC_{50}$ values (the TTPs 340, 341, and 342, $EC_{50}$=25-55 μM), each of which had a carbonyl appendage a to the tropolone oxygens that provided an alternative third contact point.

Seven HPD primary hits were found among the 24 HPDs screened. Three of these were confirmed hits, (518, 668, and 670) with $EC_{50}$ values ranging from 14-20 μM. This is insufficient to generate a meaningful SAR, but trends can be inferred. The oxygen trident of the HPD scaffold is essential for their activity as the loss of any one of these oxygens results in inactive compounds. In each case it is presumed based on data with other HPDs against HBV (Edwards et al., 2019a) that strong ionic interactions along with charge-assisted hydrogen bonds anchor the chelator moiety of HPDs (N-hydroxyimide group) to the RVFV endonuclease catalytic ensemble comprised by the two positively charged $Mg^{++}$ ions. Lastly, aromatic substitutions at the imine nitrogen are tolerated that carry modifications including halogen electron withdrawing groups and an alkyl electron donating group.

Activity in a human respiratory epithelial cell line. To assess whether RVFV inhibitors can work in human respiratory epithelia cells (a primary target tissue for the virus in people), $EC_{50}$ and $CC_{50}$ values were determined for 19 compounds in A549 cells. A549s were derived from a male lung carcinoma patient and are widely used to model lung epithelial cells. Cells were infected with RVFV and compounds were added immediately after infection at increasing concentrations. The number of RVFV foci were determined 24 hours later, and cytotoxicity was determined by measuring protease release into the culture medium using the Promega CytotoxGlo assay (Table 4). Compound 309 was added to the analysis to test the role of the S atom in the thiophene ring in 308 by substituting a furan ring. $EC_{50}$ values ranged from 5.85→90 UM and TI values ranged from <1 to ~17. The promising $EC_{50}$ value for 308 in Vero cells was not apparent in A549 cells, and substituting a furan ring for the thiophene in 308 had no effect in A549 cells because 308 and 309 had similar $EC_{50}$ values (8.4 vs. 55.8 UM). Compared to their activity in Vero cells, 8

TABLE 4

Activity in the human epithelial cell line A549.

| Compound number | $EC_{50}$ (μM) | $CC_{50}$ (μM)* | TI |
|---|---|---|---|
| 308 | 8.36 | 119.10 | 14.24 |
| 309 | 5.85 | 98.06 | 16.77 |
| 320 | 90.28 | 120 | 1.33 |
| 327 | 19.64 | 27.54 | 1.40 |
| 330 | 42.56 | 120 | 2.82 |
| 331 | 17.66 | 120 | 6.80 |
| 335 | 120 | 96.24 | 0.80 |
| 390 | 9.37 | 120 | 12.81 |
| 515 | 120 | 93.60 | 0.78 |
| 517 | 95.77 | 71.76 | 0.75 |
| 518 | 17.19 | 16.51 | 0.96 |
| 668 | 35.74 | 82.04 | 2.30 |
| 670 | 15.28 | 120 | 7.85 |
| 680 | 11.61 | 120 | 10.33 |
| 686 | 7.87 | 67.60 | 8.59 |
| 704 | 19.97 | 43.01 | 2.15 |
| 840 | 15.42 | 120 | 7.78 |
| 867 | 33.04 | 120 | 3.63 |
| 1039 | 15.52 | 120 | 7.73 |

*Arbitrary value. 120 μM is the assay upper limit.

compounds had higher $EC_{50}$s in A549 cells, 6 had equivalent values, and 4 had lower $EC_{50}$s. These differences may be due to species differences as Vero cells are from African Green Monkeys and A549s are human-derived. Regardless of the quantitative differences, 10 of the 18 compounds included in both data sets had equivalent or better $EC_{50}$s in the human line, highlighting their potential for development into drugs to treat human infections.

Mechanism of action. The mechanism(s) of action of the RVFV inhibitors are unknown and could involve inhibition of viral and/or cellular proteins. However, inhibiting one or more mono- or di-metalloenzymes needed for viral replication by chelating their active site divalent cations is a likely mechanism. The rationale for implicating metal chelation comes from the compound structures and their known activities against HIV and presumed activity against HBV (Brooks et al., 2019; Edwards et al., 2019b; Wang et al., 2018). The αHTs and HPDs have metal chelating tridents suitable for binding to the $Mg^{++}$ ions in di-metalloenzyme active sites, and they are known to work by this mechanism against the HIV ribonuclease H and/or integrase, the influenza virus PA endonuclease (Himmel et al., 2009; Omoto et al., 2018; Suchaud et al., 2012; Wang et al., 2018). The two confirmed TRP hits (341 and 342) also have a divalent cation-binding motif, although it is comprised of two adjacent oxygens that typically bind to active site cations of mono-metalloenzymes (Jacobsen et al., 2007). However, the failure of many compounds with known ability to inhibit divalent cation containing metalloenzymes (~70% of the αHTs did not inhibit RVFV growth) indicates that metal chelation by itself is insufficient, presumably because additional compound:target interactions are needed to provide sufficient binding affinity to inhibit viral replication.

Figure 3:
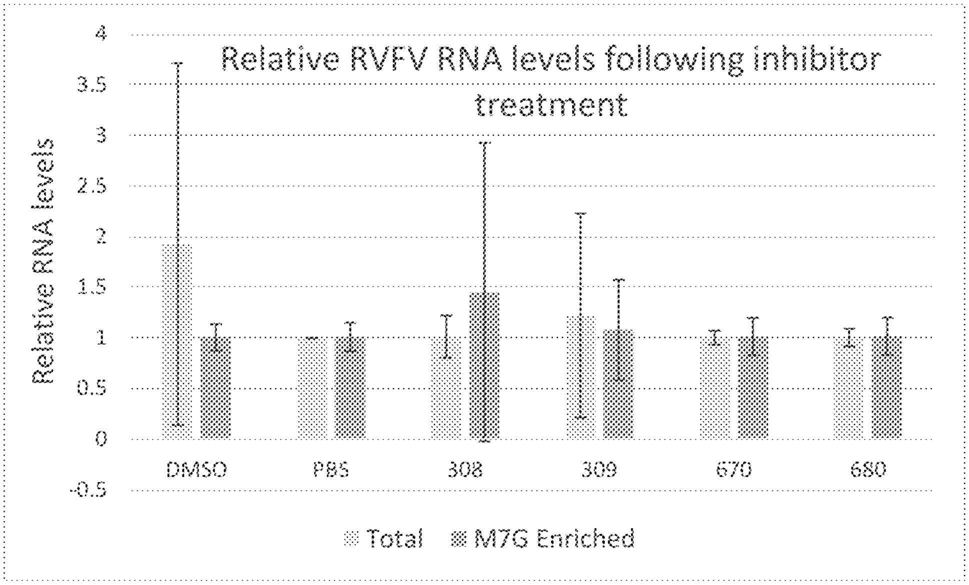
FIG. 3 shows RVFV-infected cells were treated for one day with 20 μM of representative RVFV inhibitors, intracellular RNAs were isolated, and RVFV RNA levels were measured by quantitative PCR. Total, total RVFV RNA; M7G Enriched, RNAs following immunoprecipitation with an antibody against the M7G 5' cap on the mRNA (i.e., enriched for mRNAs).

The most likely target based on the viral replication mechanism is the RVFV cap-snatching endonuclease activity of the viral L protein. This is because it is a di-metalloenzyme that catalyzes a reaction similar to that of the cap-snatching endonuclease PA endonuclease from Influenza Virus that has recently been targeted by the metal-chelating drug Baloxavir marboxil (Omoto et al., 2018). However, treatment of RVFV infected cells with representative inhibitors did not suppress either RVFV mRNAs or total RVFV RNA compared to PBS- or DMSO vehicle-treated infected cultures FIG. 3. Consequently, RNA levels do not correlate with the reduction in viral titers induced by the compounds, indicating that the target(s) of the compounds affect production of infectious virus without suppressing viral RNA accumulation.

CONCLUSIONS

Screening for RVFV replication inhibitors among compounds selected for their similarity to inhibitors of viral nucleases identified 36 novel RVFV inhibitors. The frequent efficacy of the αHT and HPD compounds screened against RVFV replication indicates that these two scaffolds are promising candidates for optimization into anti-RVFV drugs for use against human and/or veterinary infections. The mechanism(s) of action for these inhibitors are not known. Substantial cytotoxicity was observed in human hepatoblastoma cells, indicating that identifying and mitigating the causes of cytotoxicity will be key to optimizing these hits. The conservation of the cap-snatching mechanism among the bunyaviruses implies that these hits hold potential for development into treatments for other bunyaviral pathogens, including Hantaan Virus, Crimean-Congo Hemorrhagic Fever Virus, and La Crosse Virus.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods, and in the steps or in the sequence of steps of the methods described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

F. REFERENCES

The following references, to the extent that they provide exemplary procedural or other details supplementary to those set forth herein, are specifically incorporated herein by reference:

Anderson, N. G., Practical Process Research & Development—A Guide For Organic Chemists, 2nd ed., Academic Press, New York, 2012.
*March's Advanced Organic Chemistry: Reactions, Mechanisms, and Structure,* 2007.
WO 2016/201243
WO 2017/184752
Agyemang et al., *RSC Adv.,* 9:34227-34234, 2019.
Amroun et al., *Crit. Rev. Microbiol.,* 43:753-778, 2017.
Ariza et al., *Nuc. Acid Res.,* 41(11):5912-5926, 2013.
Berkowitz et al., *Tetrahedron Lett.,* 59:3026-3028, 2018.
Brooks et al., *Pharmacotherapy,* 39:576-598, 2019.
Cao et al., *ACS Omega,* 3:15125-15133, 2018.
Chen et al., *Chem. Rev.,* 119:1323-1455, 2019.
Donlin et al., *Antimicrob. Agents Chemother.,* 61:e02574-02516, 2017.
Edwards et al., *Antiviral Res.,* 164:70-80, 2019.
Edwards et al., *Expert Opin. Ther. Targets,* 23(7):559-563, 2019b.
Elliott et al., *Curr. Opin. Vir.,* 5(100):50-57, 2014.

Guo et al., *J. Virol.,* 81:12472-12484, 2007.
Hartman, *Clin. Lab. Med.,* 37:285-301, 2017.
Hazuda et al., *Annu. Rev. Pharmacol. Toxicol.,* 49:377-394, 2009.
Himmel et al., *Structure,* 17:1625-1635, 2009.
Himmel et al., *ACS Chem. Biol.,* 1:702-712, 2006.
Hirsch et al., *Bioorg. Med. Chem. Lett.,* 24:4943-4947, 2014.
Hirsch et al., *Org. Biomol. Chem.,* 16:62-69, 2017.
Methods for dilution antimicrobial susceptibility tests for bacteria that grow aerobically; Approved Standard—Tenth Edition, in: Institute, C.a.L.S. (Ed.). Clinical and Laboratory Standards Institute, Wayne, P A, 2015.
Jacobsen et al., *Inorg. Chim. Acta,* 360:264-272, 2007.
Lomonosova et al., *Antiviral Res.,* 144:164-172, 2017.
Lu et al., *Antimicrob. Agents Chemother.,* 59:1070-1079, 2015.
Masaoka et al., *Biochemistry,* 55:809-819, 2016.
Meck et al., *MedChemComm,* 5, 842-852, 2014.
Meck et al., *Org. Lett.,* 14:5988-5991, 2012.
Mehand et al., *Antiviral Res.,* 159:63-67, 2018.
Nowotny, *EMBO Rep.,* 10:144-151, 2009.
Omoto et al., *Sci. Rep.,* 8:9633, 2018.
Pflug et al., *Virus Res.,* 234:103-117, 2017.
Federal Select Agent Program, 2017. Select Agents and Toxins List. Federal Select Agents Program, p. www.selectagents.gov/SelectAgentsandToxinsList.html.
Su et al., *J. Virol.,* 84:7625-7633, 2010.
Suchaud et al., *Bioorg. Med. Chem. Lett.,* 22:3988-3992, 2012.
Villa et al., *Antiviral Res.,* 132:186-195, 2016.
Wang et al., *Curr. Med. Chem.,* 25:1682-1702, 2018.
Yang, *Ann. Pharmacother.,* 53:754-759, 2019.
Yang and Steitz, *Structure,* 3:131-134, 1995.

What is claimed:

1. A method of treating Rift Valley fever in a patient comprising administering to the patient a therapeutically effective amount of a compound according to the formula:

(I)

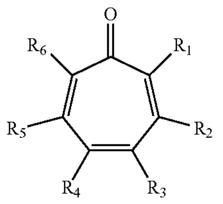

wherein:

$R_1$ is hydroxy or a group of the formula: $SC(O)R_1'$, wherein:

$R_1'$ is an amino acid residue, a protected amino acid residue, aryl$_{(C\leq12)}$, heteroaryl$_{(C\leq12)}$, aralkyl$_{(C\leq12)}$, or a substituted version of these three groups $R_2$ and $R_5$ are each independently selected from hydrogen, halo, hydroxy, aryl$_{(C\leq12)}$, substituted aryl$_{(C\leq12)}$, acyl$_{(C\leq12)}$, substituted acyl$_{(C\leq12)}$, —C(O)R', or —S(O)$_x$R'', wherein:

R' is —$X_1$—$Y_1$, wherein:

$X_1$ is alkanediyl$_{(C\leq8)}$, alkenediyl$_{(C\leq8)}$, or a substituted version thereof; and $Y_1$ is aryl$_{(C\leq12)}$, heteroaryl$_{(C\leq12)}$, or a substituted version thereof;

x is 0, 1, or 2;

R'' is alkyl$_{(C\leq12)}$, aryl$_{(C\leq12)}$, aralkyl$_{(C\leq12)}$, or a substituted version thereof;

$R_3$ is hydrogen, alkyl$_{(C\leq12)}$, or substituted alkyl$_{(C\leq12)}$;

$R_4$ is hydrogen or alkyl$_{(C\leq12)}$, cycloalkyl$_{(C\leq12)}$, aryl$_{(C\leq18)}$, heteroaryl$_{(C\leq18)}$, or a substituted version of these four groups; —C(O)$R_a$, —S(O)$_y$$R_b$, —C(O)N($R_c$)$R_d$, or

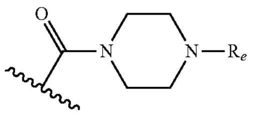

wherein:

$R_a$ is alkyl$_{(C\leq12)}$, cycloalkyl$_{(C\leq12)}$, aryl$_{(C\leq12)}$, heteroaryl$_{(C\leq12)}$, heterocycloalkyl$_{(C\leq12)}$, alkoxy$_{(C\leq12)}$, or —$X_2$—$Y_2$, wherein:

$X_2$ is arenediyl$_{(C\leq12)}$ or substituted arenediyl$_{(C\leq12)}$; and $Y_2$ is aryl$_{(C\leq12)}$, heteroaryl$_{(C\leq12)}$, or a substituted version thereof;

$R_b$ is aryl$_{(C\leq12)}$, heteroaryl$_{(C\leq12)}$, or a substituted version thereof;

$R_c$ is hydrogen, alkyl$_{(C\leq6)}$, or substituted alkyl$_{(C\leq6)}$;

$R_d$ is alkyl$_{(C\leq12)}$, cycloalkyl$_{(C\leq12)}$, aryl$_{(C\leq12)}$, heteroaryl$_{(C\leq12)}$, aralkyl$_{(C\leq12)}$, heterocycloalkyl$_{(C\leq12)}$, or a substituted version thereof, or —$X_3$—$Y_3$;

wherein:

$X_3$ is arenediyl$_{(C\leq12)}$, -alkanediyl$_{(C\leq8)}$-arenediyl$_{(C\leq12)}$, or a substituted version thereof; and $Y_3$ is aryl$_{(C\leq12)}$, heteroaryl$_{(C\leq12)}$, aralkyl$_{(C\leq12)}$, heterocycloalkyl$_{(C\leq12)}$, aralkoxy$_{(C\leq12)}$, or a substituted version thereof;

$R_e$ is aryl$_{(C\leq12)}$, heteroaryl$_{(C\leq12)}$, aralkyl$_{(C\leq18)}$, or a substituted version thereof, or a group of the formula:

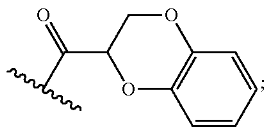
; and $R_6$ is hydroxy;

or a pharmaceutically acceptable salt of either of these formulae.

2. The method of claim 1, wherein the compound of formula (I) is further defined as:

(I)

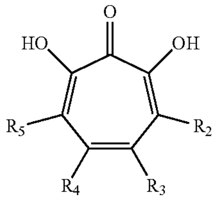

wherein:

$R_2$ and $R_5$ are each independently selected from hydrogen, halo, hydroxy, aryl$_{(C\leq12)}$, substituted aryl$_{(C\leq12)}$, acyl$_{(C\leq12)}$, substituted acyl$_{(C\leq12)}$, —C(O)R', or —S(O)$_x$R'', wherein:

R' is —$X_1$—$Y_1$, wherein:

$X_1$ is alkanediyl$_{(C\leq 8)}$, alkenediyl$_{(C\leq 8)}$, or a substituted version thereof; and $Y_1$ is aryl$_{(C\leq 12)}$, heteroaryl$_{(C\leq 12)}$, or a substituted version thereof;

x is 0, 1, or 2;

R" is alkyl$_{(C\leq 12)}$, aryl$_{(C\leq 12)}$, aralkyl$_{(C\leq 12)}$, or a substituted version thereof;

$R_3$ is hydrogen, alkyl$_{(C\leq 12)}$, or substituted alkyl$_{(C\leq 12)}$;

$R_4$ is hydrogen or alkyl$_{(C\leq 12)}$, cycloalkyl$_{(C\leq 12)}$, aryl$_{(C\leq 18)}$, heteroaryl$_{(C\leq 18)}$, or a substituted version of these four groups; —C(O)$R_a$, —S(O)$_y R_b$, —C(O)N($R_c$)$R_d$, or

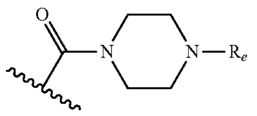

wherein:

$R_a$ is alkyl$_{(C\leq 12)}$, cycloalkyl$_{(C\leq 12)}$, aryl$_{(C\leq 12)}$, heteroaryl$_{(C\leq 12)}$, heterocycloalkyl$_{(C\leq 12)}$, alkoxy$_{(C\leq 12)}$, or —$X_2$—$Y_2$, wherein:

$X_2$ is arenediyl$_{(C\leq 12)}$ or substituted arenediyl$_{(C\leq 12)}$; and $Y_2$ is aryl$_{(C\leq 12)}$, heteroaryl$_{(C\leq 12)}$, or a substituted version thereof;

$R_b$ is aryl$_{(C\leq 12)}$, heteroaryl$_{(C\leq 12)}$, or a substituted version thereof;

$R_c$ is hydrogen, alkyl$_{(C\leq 6)}$, or substituted alkyl$_{(C\leq 6)}$;

$R_d$ is alkyl$_{(C\leq 12)}$, cycloalkyl$_{(C\leq 12)}$, aryl$_{(C\leq 12)}$, heteroaryl$_{(C\leq 12)}$, aralkyl$_{(C\leq 12)}$, heterocycloalkyl$_{(C\leq 12)}$, or a substituted version thereof, or —$X_3$—$Y_3$;

wherein:

$X_3$ is arenediyl$_{(C\leq 12)}$, -alkanediyl$_{(C\leq 8)}$-arenediyl$_{(C\leq 12)}$, or a substituted version thereof; and $Y_3$ is aryl$_{(C\leq 12)}$, heteroaryl$_{(C\leq 12)}$, aralkyl$_{(C\leq 12)}$, heterocycloalkyl$_{(C\leq 12)}$, aralkoxy$_{(C\leq 12)}$, or a substituted version thereof;

$R_e$ is aryl$_{(C\leq 12)}$, heteroaryl$_{(C\leq 12)}$, aralkyl$_{(C\leq 18)}$, or a substituted version thereof, or a group of the formula:

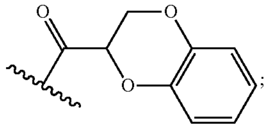

; and or a pharmaceutically acceptable salt thereof.

3. The method of claim 1, wherein $R_3$ is alkyl$_{(C\leq 12)}$ or substituted alkyl$_{(C\leq 12)}$.

4. The method of claim 1, wherein $R_2$ is hydrogen.

5. The method of claim 1, wherein $R_2$ is —S(O)$_x$R", wherein: R" is alkyl$_{(C\leq 12)}$, aryl$_{(C\leq 12)}$, aralkyl$_{(C\leq 12)}$, or a substituted version thereof.

6. The method of claim 1, wherein $R_5$ is hydrogen.

7. The method of claim 1, wherein $R_5$ is —S(O)$_x$R", wherein: R" is alkyl$_{(C\leq 12)}$, aryl$_{(C\leq 12)}$, aralkyl$_{(C\leq 12)}$, or a substituted version thereof.

8. The method of claim 1, wherein $R_4$ is —C(O)$R_a$, wherein:

$R_a$ is alkyl$_{(C\leq 12)}$, cycloalkyl$_{(C\leq 12)}$, aryl$_{(C\leq 12)}$, heteroaryl$_{(C\leq 12)}$, alkyl$_{(C\leq 12)}$, alkoxy$_{(C\leq 12)}$, or —$X_2$—$Y_2$, wherein:

$X_2$ is arenediyl$_{(C\leq 12)}$ or substituted arenediyl$_{(C\leq 12)}$; and $Y_2$ is aryl$_{(C\leq 12)}$, heteroaryl$_{(C\leq 12)}$, or a substituted version thereof.

9. The method of claim 1, wherein $R_4$ is —C(O)N($R_c$)$R_d$, wherein:

$R_c$ is hydrogen, alkyl$_{(C\leq 6)}$, or substituted alkyl$_{(C\leq 6)}$;

$R_d$ is alkyl$_{(C\leq 12)}$, cycloalkyl$_{(C\leq 12)}$, aryl$_{(C\leq 12)}$, heteroaryl$_{(C\leq 12)}$, aralkyl$_{(C\leq 12)}$, heterocycloalkyl$_{(C\leq 12)}$, or a substituted version thereof, or —$X_3$—$Y_3$;

wherein:

$X_3$ is arenediyl$_{(C\leq 12)}$, -alkanediyl$_{(C\leq 8)}$-arenediyl$_{(C\leq 12)}$, or a substituted version thereof; and $Y_3$ is aryl$_{(C\leq 12)}$, heteroaryl$_{(C\leq 12)}$, aralkyl$_{(C\leq 12)}$, heterocycloalkyl$_{(C\leq 12)}$, aralkoxy$_{(C\leq 12)}$, or a substituted version thereof.

10. The method of claim 1, wherein $R_4$ is

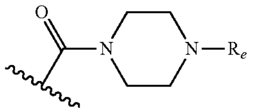

wherein:

$R_e$ is aryl$_{(C\leq 12)}$, heteroaryl$_{(C\leq 12)}$, aralkyl$_{(C\leq 18)}$, or a substituted version thereof.

11. The method of claim 1, wherein the compound is further defined as:

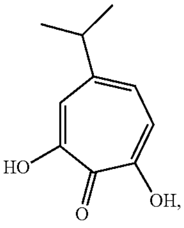

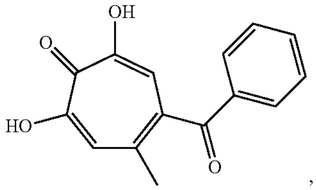

,

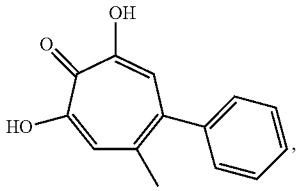

,

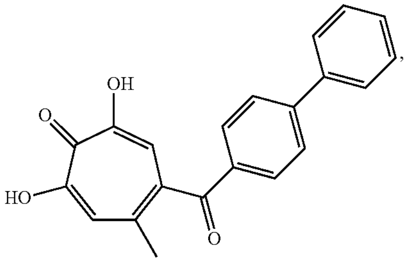

,

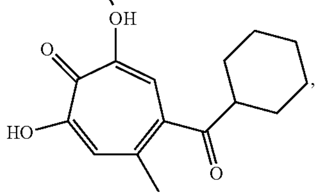

,

-continued
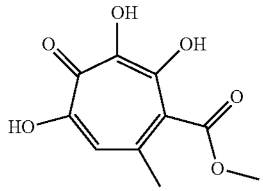,
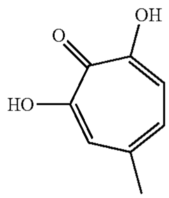,
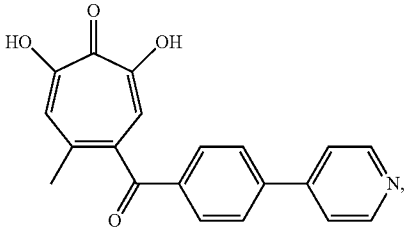
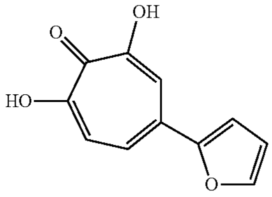,
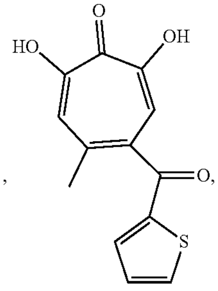
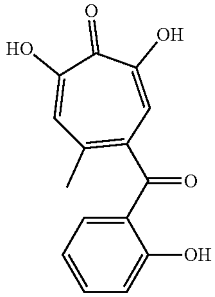,
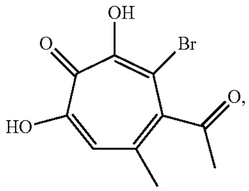
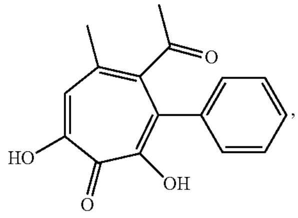
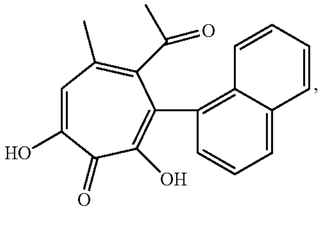
-continued
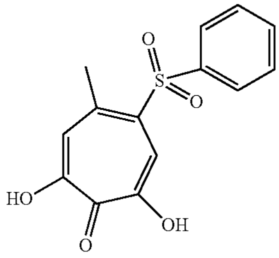,
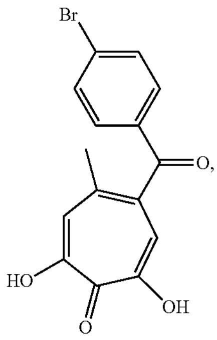
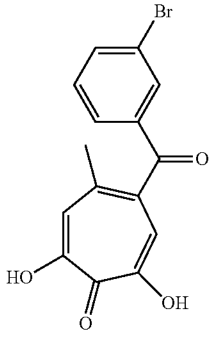,
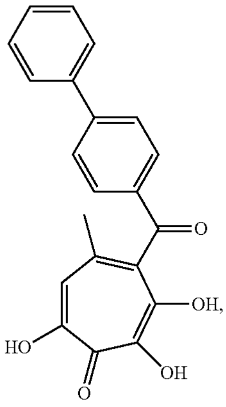
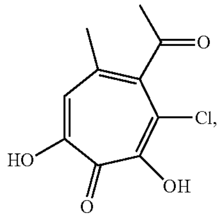
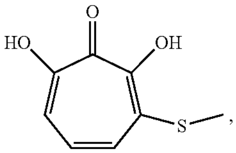
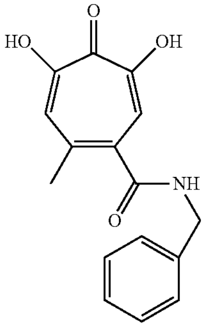,
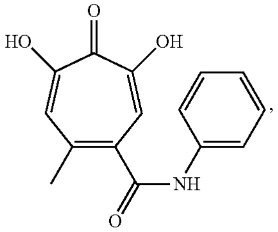
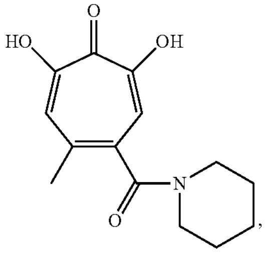

-continued

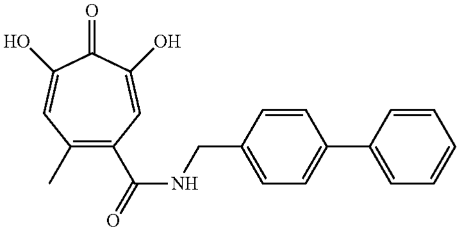

,

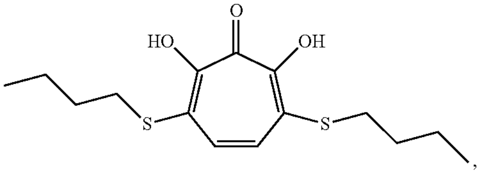

,

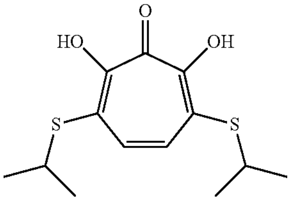

,

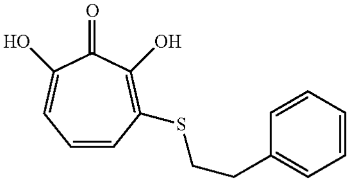

,

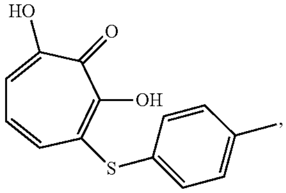

,

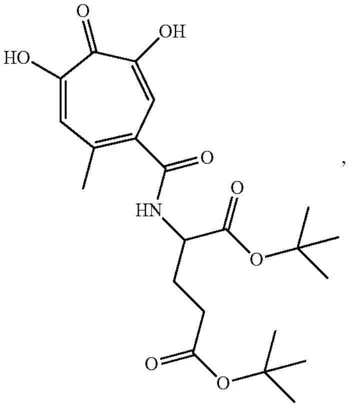

,

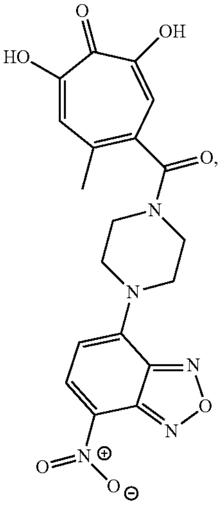

-continued

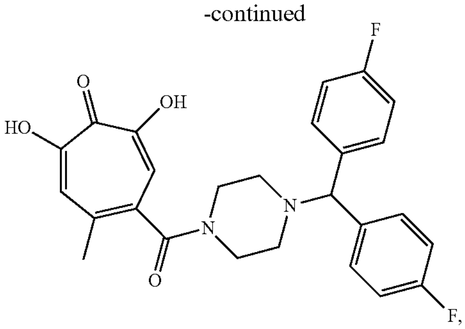

, or

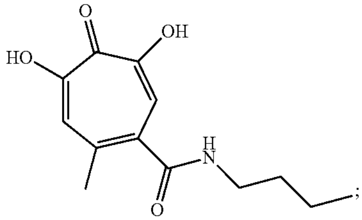

;

or a pharmaceutically acceptable salt thereof.

12. The method of claim 1, wherein the compound is administered intravenously, intraarterially, orally, buccally, nasally, ocularly, rectally, vaginally, topically, intramuscularly, intradermally, cutaneously, or subcutaneously.

13. A method of inhibiting the replication of a bunyavirus comprising contacting the bunyavirus with an effective amount of a compound according to the formula:

(I)

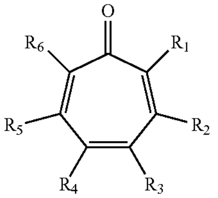

wherein:

$R_1$ is hydroxy or a group of the formula: $SC(O)R_1'$, wherein:

$R_1'$ is an amino acid residue, a protected amino acid residue, aryl$_{(C\le12)}$, heteroaryl$_{(C\le12)}$, aralkyl$_{(C\le12)}$, or a substituted version of these three groups $R_2$ and $R_5$ are each independently selected from hydrogen, halo, hydroxy, aryl$_{(C\le12)}$, substituted aryl$_{(C\le12)}$, acyl$_{(C\le12)}$, substituted acyl$_{(C\le12)}$, —C(O)R', or —S(O)$_x$R", wherein:

R' is —$X_1$—$Y_1$, wherein:

$X_1$ is alkanediyl$_{(C\le8)}$, alkenediyl$_{(C\le8)}$, or a substituted version thereof; and $Y_1$ is aryl$_{(C\le12)}$, heteroaryl$_{(C\le12)}$, or a substituted version thereof;

x is 0, 1, or 2;

R" is alkyl$_{(C\le12)}$, aryl$_{(C\le12)}$, aralkyl$_{(C\le12)}$, or a substituted version thereof;

$R_3$ is hydrogen, alkyl$_{(C\le12)}$, or substituted alkyl$_{(C\le12)}$;

$R_4$ is hydrogen or alkyl$_{(C\le12)}$, cycloalkyl$_{(C\le12)}$, aryl$_{(C\le18)}$, heteroaryl$_{(C\le18)}$, or a substituted version of these four groups; —C(O)$R_a$, —S(O)$_y$$R_b$, —C(O)N($R_c$)$R_d$, or

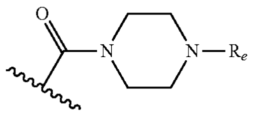

wherein:

$R_a$ is alkyl$_{(C\leq 12)}$, cycloalkyl$_{(C\leq 12)}$, aryl$_{(C\leq 12)}$, heteroaryl$_{(C\leq 12)}$, heterocycloalkyl$_{(C\leq 12)}$, alkoxy$_{(C\leq 12)}$, or —$X_2$—$Y_2$, wherein:

$X_2$ is arenediyl$_{(C\leq 12)}$ or substituted arenediyl$_{(C\leq 12)}$; and $Y_2$ is aryl$_{(C\leq 12)}$, heteroaryl$_{(C\leq 12)}$, or a substituted version thereof;

$R_b$ is aryl$_{(C\leq 12)}$, heteroaryl$_{(C\leq 12)}$, or a substituted version thereof;

$R_c$ is hydrogen, alkyl$_{(C\leq 6)}$, or substituted alkyl$_{(C\leq 6)}$;

$R_d$ is alkyl$_{(C\leq 12)}$, cycloalkyl$_{(C\leq 12)}$, aryl$_{(C\leq 12)}$, heteroaryl$_{(C\leq 12)}$, aralkyl$_{(C\leq 12)}$, heterocycloalkyl$_{(C\leq 12)}$, or a substituted version thereof, or —$X_3$—$Y_3$;

wherein:

$X_3$ is arenediyl$_{(C\leq 12)}$, -alkanediyl$_{(C\leq 8)}$-arenediyl$_{(C\leq 12)}$, or a substituted version thereof; and $Y_3$ is aryl$_{(C\leq 12)}$, heteroaryl$_{(C\leq 12)}$, aralkyl$_{(C\leq 12)}$, heterocycloalkyl$_{(C\leq 12)}$, aralkoxy$_{(C\leq 12)}$, or a substituted version thereof;

$R_e$ is aryl$_{(C\leq 12)}$, heteroaryl$_{(C\leq 12)}$, aralkyl$_{(C\leq 18)}$, or a substituted version thereof, or a group of the formula:

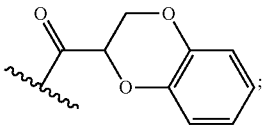

; and $R_6$ is hydroxy;

or a pharmaceutically acceptable salt thereof.

14. The method of claim 13, wherein the bunyavirus is Rift Valley phlebovirus.

15. The method of claim 13, wherein the bunyavirus is orthohantavirus.

16. The method of claim 13, wherein the bunyavirus is La Crosse arbovirus.

17. The method of claim 13, wherein the bunyavirus is Crimean-Congo hemorrhagic fever orthoairovirus.

* * * * *